United States Patent [19]
Haralambopoulos

[11] Patent Number: 5,314,653
[45] Date of Patent: May 24, 1994

[54] UNIFORMLY EXPANDABLE MOLD AND METHOD

[75] Inventor: Constantine Haralambopoulos, Rochester, N.Y.

[73] Assignee: Harold Gell, P.C., Silver Spring, Md.

[21] Appl. No.: 964,285

[22] Filed: Oct. 21, 1992

[51] Int. Cl.⁵ .................................................. B29C 41/14
[52] U.S. Cl. ....................................... 264/301; 264/308; 264/313; 264/314; 425/271; 425/275; 425/DIG. 14; 425/DIG. 44; 427/2; 427/171
[58] Field of Search ............... 264/301, 305, 306, 308, 264/313, 314, 255, 291; 425/269, 271, 275, DIG. 14, DIG. 44; 427/2, 171

[56] References Cited

U.S. PATENT DOCUMENTS

| | | | |
|---|---|---|---|
| 663,634 | 12/1900 | Mitzell | 264/305 |
| 1,994,317 | 3/1935 | Linscott | 425/275 |
| 2,328,769 | 9/1943 | Auzin | 425/269 |
| 2,518,326 | 8/1950 | Ingram | 425/271 |
| 4,266,750 | 5/1981 | Gallizia | 425/DIG. 14 |
| 4,626,250 | 12/1986 | Schneider | 604/352 |
| 4,637,907 | 1/1987 | Hegel et al. | 425/269 |
| 5,059,486 | 10/1991 | Maronian et al. | 264/288.4 |
| 5,069,227 | 12/1991 | Maronian | 427/2 |
| 5,113,874 | 5/1992 | Maronian | 427/2 |

FOREIGN PATENT DOCUMENTS 0365024 4/1990 European Pat. Off. .
WO91/00180 1/1991 World Int. Prop. O. .

Primary Examiner—Jay H. Woo
Assistant Examiner—Robert B. Davis
Attorney, Agent, or Firm—Harold Gell

[57] ABSTRACT

A uniformly expandable mold is formed with a continuous surface defining a three-dimensional pattern for replicating an article. The relative pressure between the inside of the mold and the outside controls the area of the surface to change the size of the three-dimensional pattern without distorting the relative dimensional relationship of the component segments forming the pattern whereby material may be deposited on the mold surface with the mold expanded to a desired size. The pressure differential is increased to increase the size of the mold and stretch the layer already deposited thereon. A second, dissimilar layer is bonded to the first layer while it is streched When the article is removed from the mold, a state of relative expansive/compressive tension is created at the bond interface between the first and second layers which forces the material of one layer to enter voids in the other layer to seal defects.

17 Claims, 15 Drawing Sheets

UNIFORMLY EXPANDABLE MOLD AND METHOD

STATEMENT OF INVENTION

This invention relates to expandable molds and methods of using them for making shaped, thin-walled, elastic articles and devices; and the devices thus made. More particularly, the invention relates to such improvements whereby the molds are uniformly expandable and they are used to:

(a) stretch-coat finished, shaped articles and devices for rendering them self-healing", i.e., more imperforate and less subject to leakage of fluids during use, despite repeated elastic stretching and relaxing;

(b) minimize manufacturing defects in the articles and devices during their pre-cure manufacturing stage;

(c) facilitate removal of undesirable soluble substances from the finished articles or devices, and (d) enable on-line electrical testing of the finished articles or devices in their stretched (expanded) state.

This invention is co-pending with U.S. Patent Applications titled "UNIFORMLY EXPANDABLE MOLD FOR A PROPHYLACTIC DEVICE HAVING PATHOGEN RESISTANT BARRIER AND METHOD" Ser. No. 07/964,096 filed Oct. 21, 1992 and "UNIFORMLY EXPANDABLE MOLD FOR A SELF-HEALING RUBBER ARTICLE AND METHOD" Ser. No. 07/964,287 filed Oct. 21, 1992.

BACKGROUND OF PRIOR ART

In the past, thin layers, sheets, and films of natural latex rubber have been widely used for a variety of different products, ranging from decorative articles, protective devices, and many different kinds of medical devices. Such thin rubber articles are often made in seamless form by dipping or otherwise coating a shaped, rigid mold of fixed dimensions, into a liquid latex solution and curing the resulting shaped rubber article.

A large proportion of such manufactured articles are often defective and unusable for their intended purposes, due to the formation of small openings, e.g., pin holes, in the rubber film, as well as thin spots, or weakened areas in the thin rubber layer. Such small openings become enlarged during elastic stretching of the article, and sometimes burst; as does the thin film in the thin spots or weakened areas as the rubber article is stretched.

As a result, such manufacturing imperfections result in undesirably large rejection rates of the resulting products, that in some instances exceed more than 10% of the yield. Particularly in the medical product uses, such imperfections render the articles unsuitable, permitting contaminated body fluids to leak through the small openings in the rubber layer and resulting in the possibility of transmitting infection to persons in contact with the rubber articles.

The mold and techniques disclosed herein provide a method whereby a rubber article is rendered "self-healing" by stretch-coating the article on an "expandable mold". However, the prior art does not teach making such a mold, so that the article can be stretched uniformly (proportionally) in three dimensions, as that would be the case for a shaped (hollow) article. Neither does the prior art disclose a method or apparatus for minimizing the occurrence of the above-mentioned defects in the pre-cure manufacturing stage.

In addition, the mold and techniques disclosed herein provide a method whereby an elastic prophylactic device or the mold of the present invention may be coated with a continuous thin layer of a ductile metal while the device is stretched over a mold. The resulting device can be repeatedly expanded and contracted without fracture or breaking of the thin metal layer.

The physical realities which are encountered in developing a mold to be used to create the above described objects are unique to the process and this invention. For instance, when a shaped, hollow elastic article is sufficiently pressurized to be inflated, the article does not inflate uniformly and proportionally to its shape in its relaxed, uninflated state, but it balloons out, tending to assume a spherical shape. This is the case, for example, with a latex medical glove, or any rubber glove, regardless of its thickness. An additional appreciation of the problem is gained by the experiment wherein two identical rubber balloons, inflated to two different diameters are connected with a tube, whereupon air rushes from the balloon of the smaller diameter to the other of the larger diameter. The quantitative relationship among pressure (P), tension (T) (defined as the force over proportional elongation), and the radius (R) of an inflated elastic sphere is given by the formula:

$$P = \frac{2T}{R}. \qquad (1)$$

For an elastic cylinder the formula is:

$$P = \frac{T}{R}. \qquad (2)$$

These formulas are known as "Laplace's law". Consequently, the intuitive approach to making an expandable mold, of an arbitrary shape, out of an elastic envelope having different curvatures at different regions of its surface, and which can be uniformly expanded (inflated), is precluded by Laplace's law. Only when the elastic envelope has a spherical shape (i.e., a single radius of curvature) and a substantially uniform wall thickness, proportional expansion is possible.

A disadvantage of using customary rigid formers (molds) for making shaped elastic devices, such as latex medical gloves and prophylactics, by the conventional dipping technique, is that the rigid molds cannot be used to prevent or correct the occurrence of manufacturing defects, such as pinholes and thin spots. A rigid mold serves merely as a passive support on which the thin latex film forms, and therefore, it cannot modify the latex film, once formed, in any way.

Natural latex rubber is the most widely used material for many different kinds of protective and medical devices. Latex, however, contains certain undesirable, water soluble proteins which become entrapped in the elastomeric matrix of the finished (vulcanized) devices. Such proteins leach out of the devices in contact with human tissues during their intended use. As reported in the Food and Drug Administration Medical Alert letter of Mar. 29, 1991, such leachable proteins can cause adverse reactions and deaths. The current guidelines to manufacturers for deproteinization of finished latex devices call for their immersion in leaching tanks at elevated temperatures and post-cure processing wherein the devices are washed off-line with hot water.

Also, for surface treatment of the cured latex devices with chlorine or other agents which may denature surface constituents such as water soluble proteins to render them harmless. These deproteinization treatments are performed while the latex devices are off their molds and in their relaxed (unstretched) state which cannot facilitate in any way a more efficient removal of solubles from the finished device.

Currently, "dipped" latex devices, such as medical gloves and condoms, are tested for the integrity of their continuous thin latex membrane to provide an opening-free continuous barrier to pathogens, by two methods:

(a) on-line, wherein the ionic current through the devices is monitored while the devices are still on their rigid, electrically conductive, molds;

(b) off-line, wherein a small percentage of the finished devices is selected, by statistical sampling techniques, and the devices are filled with a specified amount of water and are checked for leaks. In their stretched state they may also be tested electrically.

The prior art does not provide a method by which on-line testing of the finished devices is performed with simultaneous three-dimensional stretching of the devices. These are the conditions under which pinholes and other manufacturing defects are enlarged and become evident in seemingly intact devices. Such defects may not be detected in either the off-line or on-line tests such as electrical tests when the products are in their unstretched state.

An additional disadvantage of rigid molds conventionally used in the manufacture of dipped latex devices is that they are subject to damage with dents and scratches, producing defective devices.

SUMMARY OF INVENTION

In accordance with the present invention, a Uniformly Expandable Mold is provided, wherein the extensibility of the mold's outer elastic envelope to a requisite shape, size, and extent, is controlled by:

(a) varying the wall-thickness profile of the envelope; and/or, (b) selecting the limits of the linear elastic range of the envelope's material; and/or, (c) providing under the envelope an inflatable, non-extensible liner; and/or, (d) filling the mold cavity with on open-cell foam rubber body in adhesive contact with the inner surface of the envelope, in the expanded state of the mold.

By utilizing the expandable property of the mold, an article, which may be the mold itself, is stretch-coated with a ductile metal to render the external surface of the article or mold envelope conductive. In a preferred UEM manufacturing process, an elastic membrane is initially stretched to the extent of its intended use and a continuous coating of highly ductile metal is applied to the stretched membrane to seal its surface. In an alternate preferred UEM manufacturing process, the stretched membrane is coated with an additional elastic material and the resulting coated device permitted to relax, forming a pattern of wrinkles on its surface. The thin ductile metal layer is then applied to the wrinkled surface to form a correspondingly wrinkled metal layer that can be expanded and contracted without fracture or breaking. In another alternate preferred UEM manufacturing process, the surface of the membrane is embossed or patterned in a configuration of undulations or wrinkles. It is then coated with a thin layer of highly ductile metal to provide an expandable metal electrode or seal.

The method aspects facilitated by the Uniformly expandable Mold (UEM) include:

(a) rendering shaped rubber devices "self-healing";

(b) minimizing pinholes and thin spots in rubber latex dipped devices during the pre-cure stage;

(c) removal of solubles from finished, latex devices; and (d) on-line electrical testing of finished, latex devices in their stretched state.

The expandable properties of the UEM mold enable manufacturing processes in which a shaped elastic article is formed on the mold, expanded or stretched in three dimensions, and then coated with an elastic layer such as a thin rubber to form an overlayer. The overlayer bonds to the base layer so that when the article is relaxed and removed from the UEM mold, the relatively thicker base layer places the overlayer in a state of compression to close and seal micropores or pinholes that may have been formed in the base layer. This compression of the overlayer creates a differential stressing of the two layers at their interface which provides a "self-healing" of the multilayer article to close any small opening or pin holes that may be developed in the article during use.

BRIEF DESCRIPTION OF THE DRAWINGS

The preferred embodiments of this invention will be described with references to the figures wherein.

DETAILED DESCRIPTION OF PREFERRED EMBODIMENTS

Figure 1:
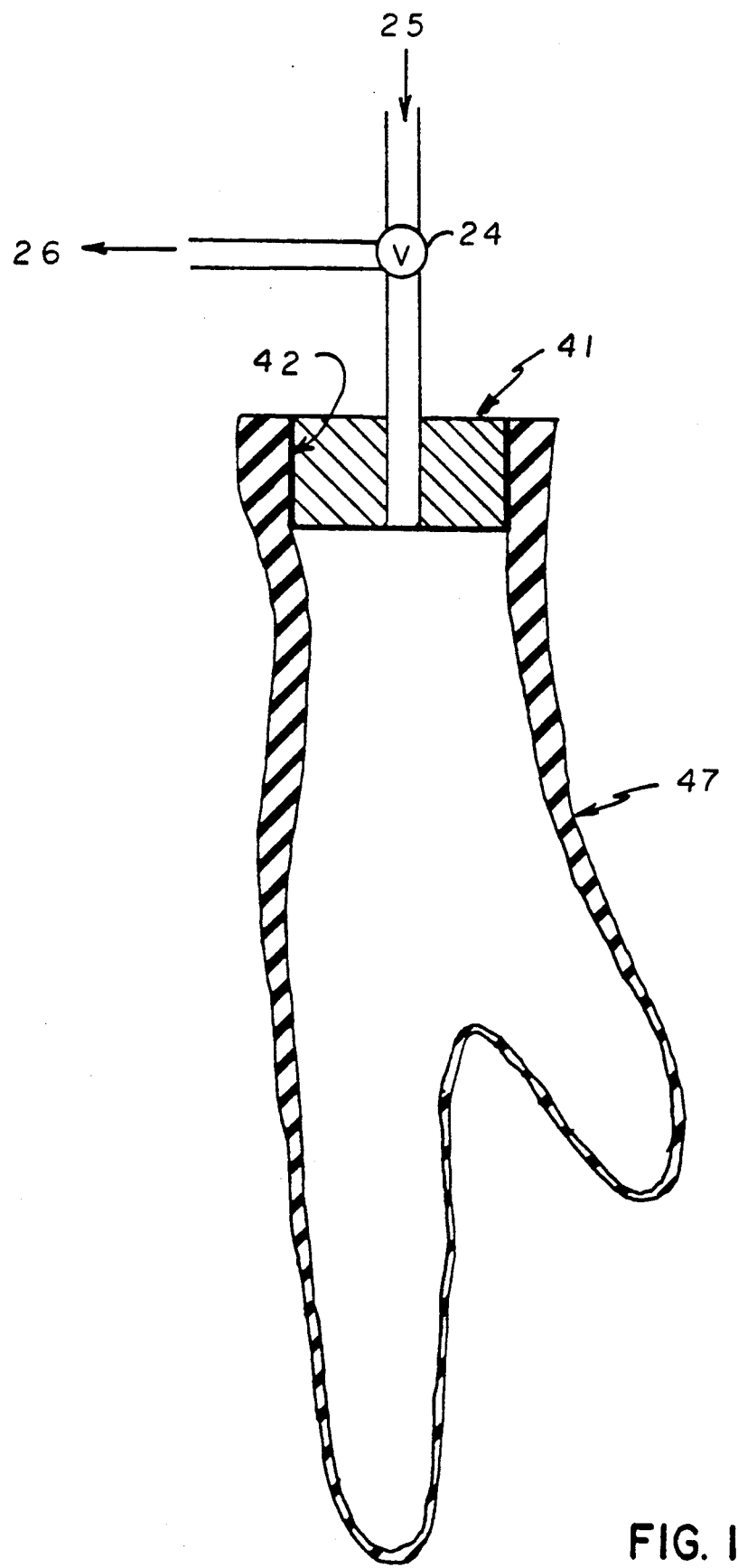
FIG. 1 is a longitudinal cross-section view of a glove-shaped UEM having a profiled expandable envelope.

In the embodiment of FIG. 1 the elastic expandable envelope of the UEM is shown schematically as a longitudinal cross section of a glove of varying wall thickness. Its wall thickness profile varies so that:

$$\frac{h}{R} = \text{constant}. \quad (3)$$

at every region of the envelope's outer surface, where (h) is the wall thickness at a region and (R) is the radius of curvature of that region. Equation (3) is equivalent to:

$$\frac{T}{R} = \text{constant}. \quad (4)$$

where (T) is the varying tension over a corresponding region of curvature of radius (R), as for the same elastomeric material, within the linear elastic range of the material, tension (T) is a constant, proportional to the thickness (h) of the material in that region.

Thus upon pressurization of the mold, its envelope expands in such a way that, within the (linear) elastic limit of the envelope's elastomeric material, the rate of change of local radii of surface curvature is the same for the entire envelope. In other words, the mold envelope expands uniformly.

In FIG. 1 the glove-shaped elastomeric envelope of the UEM is glued onto mounting block 41 around glued area 42. The mounting block is connected with a tube to a three-way valve 24, which connects the hollow space of the envelope to a pneumatic or hydraulic pressure source 25, or to ambient atmospheric pressure 47, or seals the tube to maintain the pressure inside the envelope.

Figure 2:
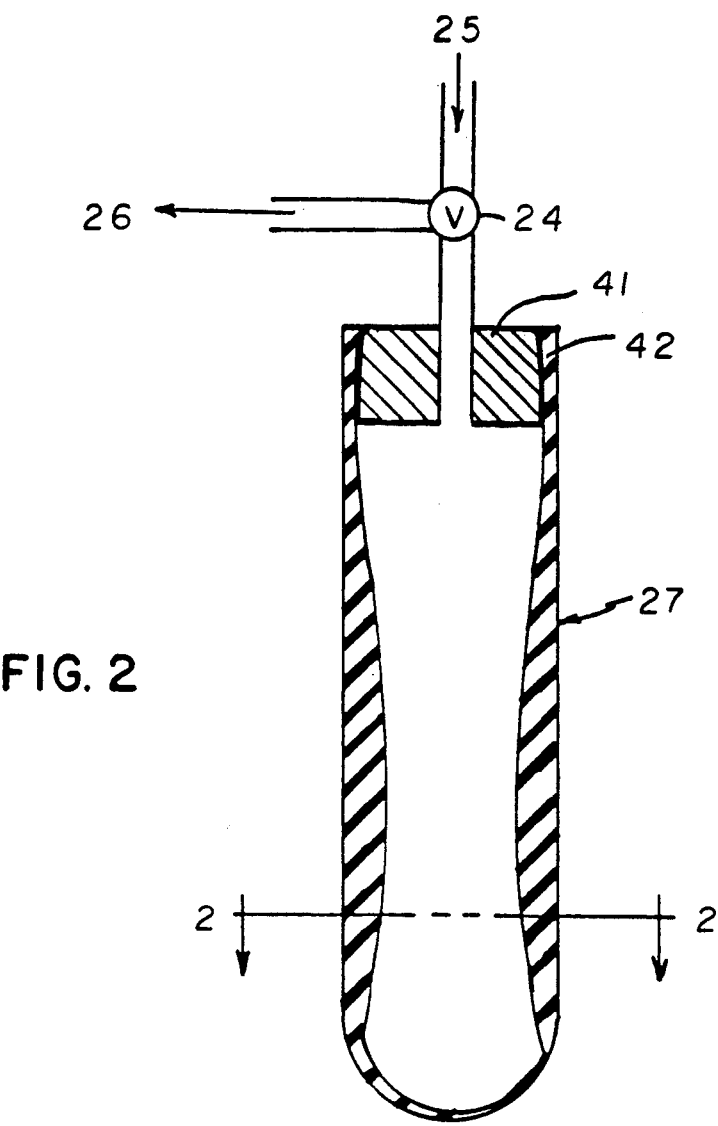
FIG. 2 is a longitudinal cross-section view of a test tube shaped UEM having a profiled expandable envelope.

Similarly, FIG. 2 shows a UEM whose expandable elastomeric envelope 27 has the shape of a common test tube for simplification. Its operational elements are identical to those of FIG. 1. The profile of cross-section of the wall of the envelope 27 is shown exaggerated to col. 6

In practice it is difficult to calculate beforehand the wall thickness profiles for a mold envelope corresponding to a device having a complex shape of varying curvature, such as that of a glove. Even for a truly cylindrical envelope closed at one end by a semi-spherical surface, profiling the wall thickness is a trial-and-error exercise. These difficulties may be due to the fact that the elastomeric material does not behave isotropically and that the finished device to be profiled does not have a uniform wall thickness to begin with. Thus, profiling a UEM envelope is an empirical process. Starting, for example, with a latex medical glove in the arrangement shown in FIG. 1, layers of latex or a silicone rubber are "painted" by a small brush, each layer is vulcanized and then pressurized to check the results. Finally, when a final desirable uniform expandability of the envelope is reached, the glove is dismounted from the block (on which it is advantageously secured by a mechanical fastening collar instead of a glue) and turned inside-out, so that its exterior side presents a smooth surface. This profiled glove can then be used as a master to make replicas, by any well-known molding method, using a suitable elastomeric material. One such material is Dow Corning Silastic 595 HC, a two-part liquid silicone rubber, having a high tensile strength and elongation (SILASTIC is a trade name of the Dow Corning Company)".

It has been found that even though an elastomer different than that of the initial envelope is used for profiling the initial envelope (e.g. a finished latex medical glove), the replica of the profiled device cast in a single elastomer exhibits substantially the same expandability characteristics of the "composite", two elastomer prototype.

With respect to a test-tube shaped envelope shown (exaggerated) in FIG. 2, it was found that the straight cylindrical walls have to be profiled with gradually "bulging" walls. The "bulging" side is inside the UEM envelope, so that its exterior surface is cylindrical.

Figure 2A:
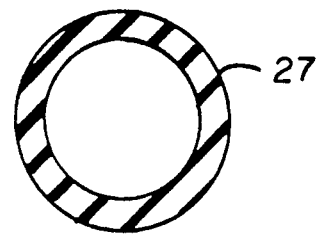
FIG. 2a is a cross-section of FIG. 2 along line 2-2.

FIG. 2a is a cross-section of FIG. 2 along line 2-2.

FIG. 2A in the envelope wall of the UEM is profiled in thickness.

The UEMs shown in FIG. 1 and FIG. 2 can be used as "formers" (molds), with the dipping process, for example, to make latex gloves and condoms, respectively. And, also, to stretch a finished device, of corresponding shape, over the UEM by fastening the device around block B with a fastener (not shown) in order to stretch-coat the device for rendering it "self-healing" or for metalizing it as described in this patent. If vacuum metallization is used, the 3-way valve 24 can admit and maintain in the hollow envelope a pressure equal to an atmosphere, or less, depending on the thickness of the envelope material used and the degree of expansion desired. Alternatively, a low vapor pressure fluid, such as a silicone oil, can be used instead of air for pressurization.

Additionally, the UEM itself may be stretch-coated with a thin metal layer in order to make the entire surface of its expandable elastomeric envelop electrically conductive. Such an electrically conductive UEM can be used in on-line electrical testing of dipped latex devices, as explained further below.

Figure 3:
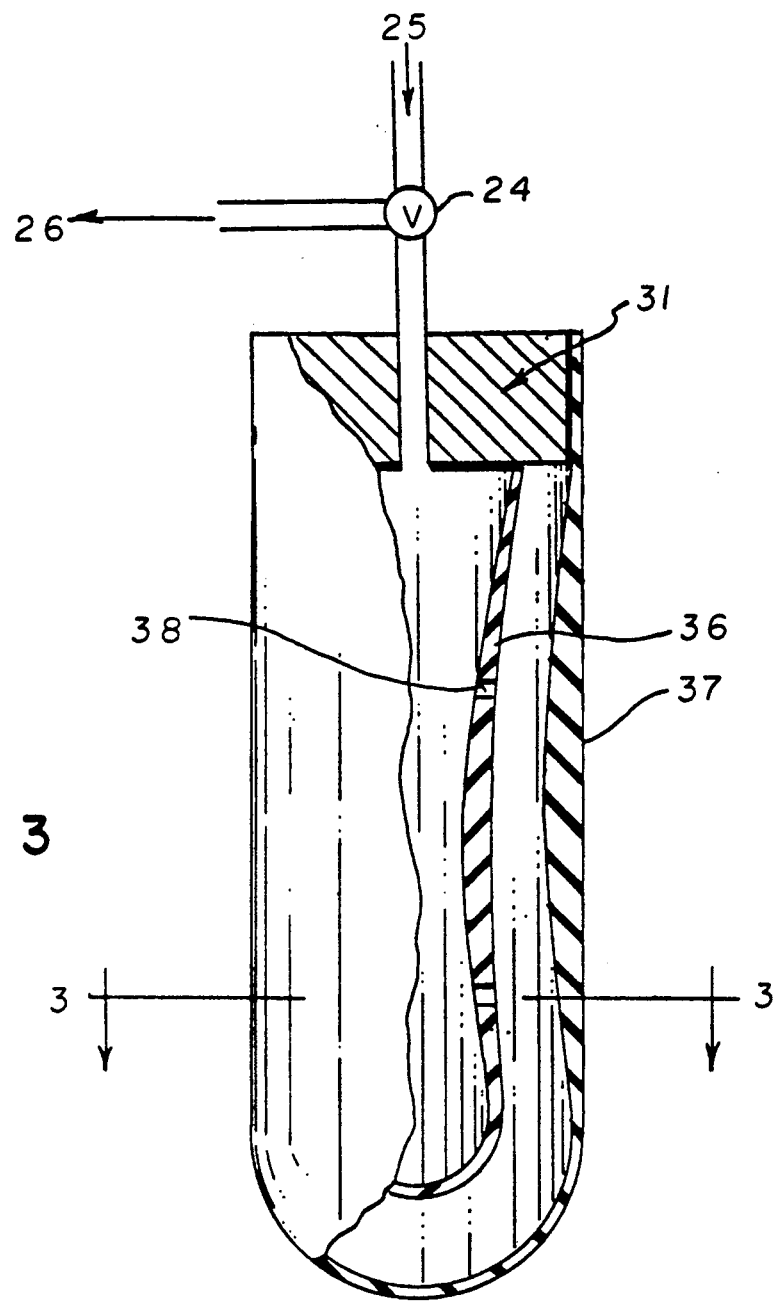
FIG. 3 is a cut-away longitudinal view of a test tube shaped UEM illustrating the wall thickness profile of the expandable envelope and a rigid perforate core.

The embodiment shown in FIG. 3 is a modification of the embodiment shown in FIG. 2. This embodiment additionally provides a rigid core 36, rigidly connected to the mounting block 31 of the UEM. The rigid core 36 is surrounded by the profiled envelope 37. The core 36 is shown as a perforate test-tube form, having opening (perforations), 38. The core 36 can be made of metal or a rigid plastic, and its purpose is to provide additional mechanical stiffness to the UEM, which is an advantageous property of the mold in particular with the dipping process. Preferably, the profiled envelope 37 in its relaxed state, fits snugly and conformally over the core 36.

Figure 3A:
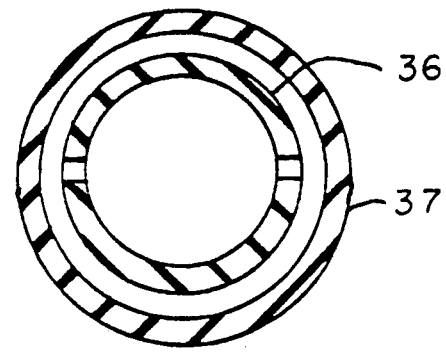
FIG. 3a is a cross-section of FIG. 3 along line 3-3.

FIG. 3a is a cross-section of FIG. 3 along line 3–3. In FIG. 3a of this embodiment is comprised of (proceeding from the outside of the mold to its inside) a profiled envelope 37 and a core 36.

The glove-shaped UEM shown in FIG. 1 can also be made according to the embodiment in FIG. 3, by providing the appropriately shaped rigid, hollow form in close contact and conformal to the inner surface of envelope 37.

Figure 4:
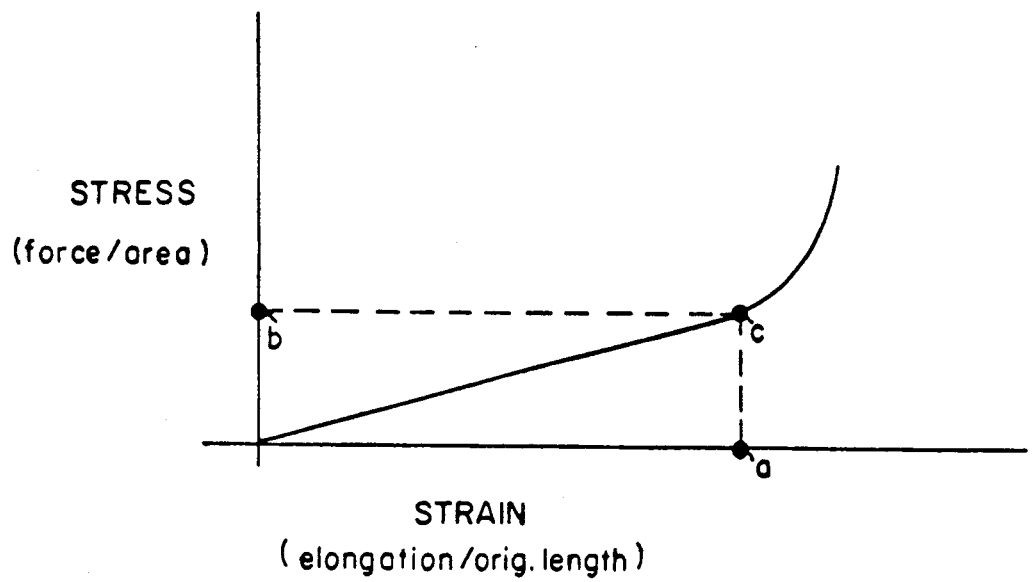
FIG. 4 is a stress vs. strain graph of a typical elastomer.

When elastomeric materials are progressively stretched, exhibit, in general, a behavior depicted by the stress vs. strain graph on FIG. 4. "Stress" is defined as the tensile force applied to a specimen over a cross-sectional area; "strain" is defined as the proportional deformation (elongation) of the specimen. In the straight line section (oc) of the curve, the elastomer behaves in a linear fashion (cf. Hooke's law), whereas beyond point (a) on the abscissa, the forces required to produce the same proportional elongation increase exponentially. An unrestrained elastic envelope expands according to the above mentioned Laplace's law in the linear region (ob) of the curve.

It has been found that when an elastomeric envelope of an arbitrary hollow shape is progressively inflated to unrestrainedly expand slightly beyond point (a), the shape of the expanding envelope tends to become proportional (similar) to its original unpressurized (smaller size) shape. Also, that the steeper and more abrupt the curve is at and beyond point (c), the closer the approximation is. This is the reason rubber toy balloons that are dip-coated in tubular shapes can be inflated to elongated, sausage-like shapes.

Figure 6:
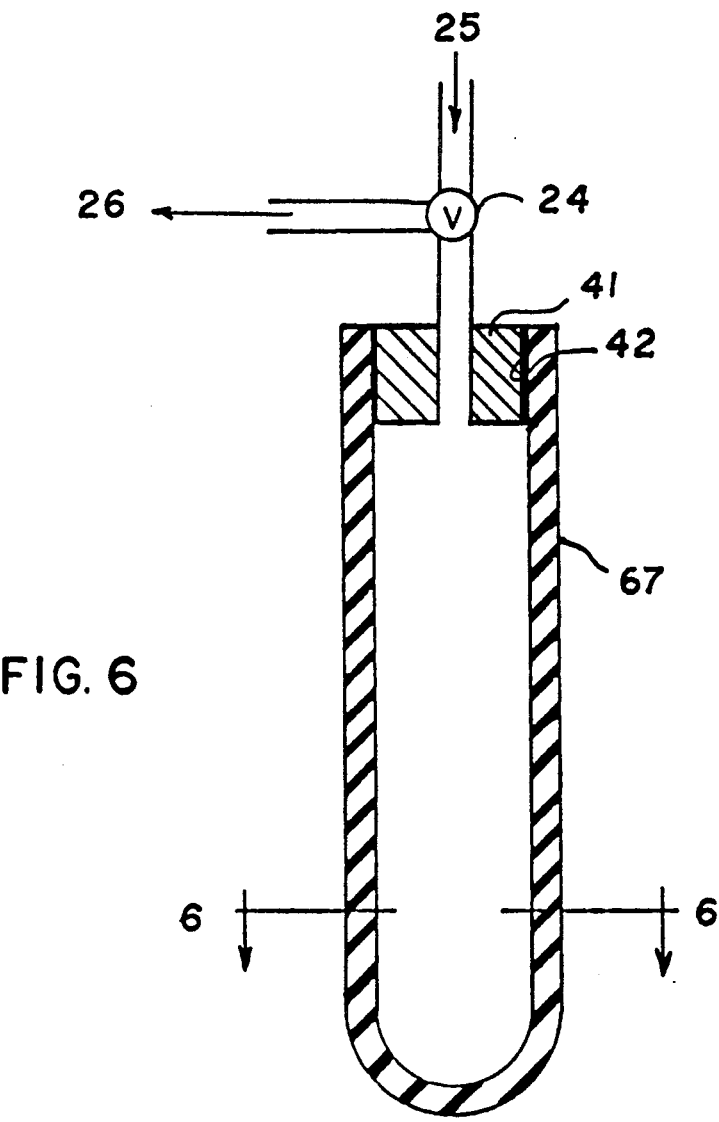
FIG. 6 is a longitudinal cross-sectional of an embodiment of a UEM having a non-linear expandable envelope shown with the envelope in its non-expanded state.
Figure 7:
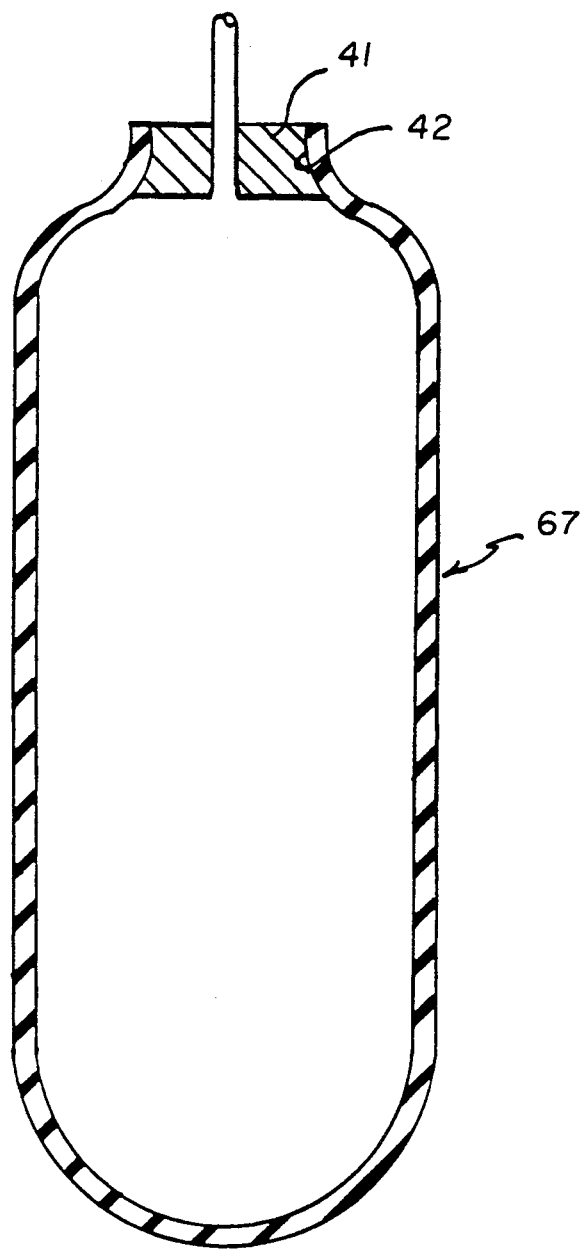
FIG. 7 is a longitudinal cross-sectional view of the UEM embodiment illustrated in FIG. 6 shown with the envelope in its expanded state.

This reversible, elastic transition property of elastomeric materials is utilized for enablement of the UEM embodiment shown relaxed in FIG. 6 and expanded in FIG. 7. In this embodiment the UEM is shown as a common test tube shaped elastomeric envelope 67, and it is arranged for pressurization as in the previous embodiments.

Initially, upon pressurization, the unrestrained envelope expands freely forming a noticeable "bulge" in its middle. However, as the pressure increases, the expanded envelope takes on a more tubular shape to eventually resemble its test tube shape before inflation.

There is a region of pressures in which the size of the expanding envelope seems not to change. Beyond that region the envelope distorts in shape and it eventually bursts. Accordingly, the working operational range of such a UEM envelope (referred to hereinafter as a non-linear envelope and by the letter symbol [E*]) of this embodiment corresponds to an expansion limit slightly beyond point (c) on its curve. In this narrow region the envelope does not appreciably exceed its elastic limit, and it assumes a predetermined size, and it returns to its original size and shape after hundreds of successive inflation/deflation cycles.

In designing such a non-linear UEM envelope, first the desired expansion of the envelope, in terms of its desired percent elongation, is selected. Then an elastomer having the requisite tensile strength is selected and compounded with an inert filler, for example, so that its new % elongation (lower in value) matches the one desired. In general, when an elastomer's modulus of elasticity is modified (i.e., increased) by an inert filler, the filler elastomer exhibits a more abrupt transition to the non-linear elastic region, compared to that of the elastomer without the filler.

Then the uniform thickness of the envelope walls is selected, which determines the overall mechanical strength of the UEM and its capacity to expand for stretching an elastic device conformally fitted and secured on the UEM. The elastic device to be stretched restrains the expandable UEM envelope and modifies its characteristics of unrestrained expansion. Therefore the UEM envelope is preferable made of at least three (3) times thicker than the device to be stretched, for a substantially proportional expansion of the UEM envelope. This design parameter is based on a test tube shape envelope whose hemispherical closed end has the same radius of curvature as the cylindrical portion of the envelope. In general, the greater the difference between any two radii of curvature on the envelope, the greater the inflation pressure has to be in order for the region of the smaller radius of curvature to reach the non-linear transition point (c). With increasing pressure there is the danger of a region of larger radius of curvature to be "pushed" far beyond point (c) into the non-linear region of the elastomer, irreversibly deforming the envelope.

Accordingly, in another embodiment (not shown) a non-linear elastomeric envelope of the UEM is additionally profiled in its wall thickness, so that the UEM can accommodate for uniform stretching elastic devices of complex shapes and with widely differing radii of curvature. Such a device is a dipped latex medical glove.

One elastomeric material that is particularly suitable for constructing a non-linear UEM envelope (of uniform thickness or profiled) is Down Corning Liquid silicone rubber, SILASTIC 595-HC a two-part liquid silicone rubber, having a high tensile strength and elongation. This elastomer is primarily used for injection molding of precision parts, including molded bellows. It has a high tensile strength (1,000 psi) and an elongation of 450%. By the addition of fumed silica or carbon black its elongation can be made as low as 5%, without diminishing its tensile strength. It was found that envelopes cast in SILASTIC 595-HC, having a diameter of 2 inches, length of 7 inches and a hemispherical closed end of radius of 1 inch, the most optimum design and operation parameters were as follows:

(a) wall thickness of 1/16 inch to ⅛ inch;

(b) percent elongation to point (a), approximately 20% (FIG. 4);

(c) inflation pressure in the range 5 psi to 8 psi.

It was also found that the non-linear elastomeric envelopes were sensitive (i.e., non-uniform expansion to variations in their wall thickness) due to the injection mold size tolerances, and that profiling the finished envelopes substantially removed their non-uniform expansion due to such variations.

Figure 6A:
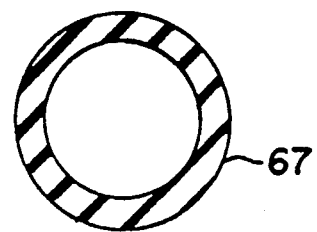
FIG. 6a is a cross-section of FIG. 6 along line 6-6.

FIG. 6a is a cross-section of FIG. 6 along line 6–6. In FIG. 3 the elastomeric material of the UEM envelope operates in the non-linear transition region of the elastomer stress vs. strain curve (FIG. 4).

Figure 8:
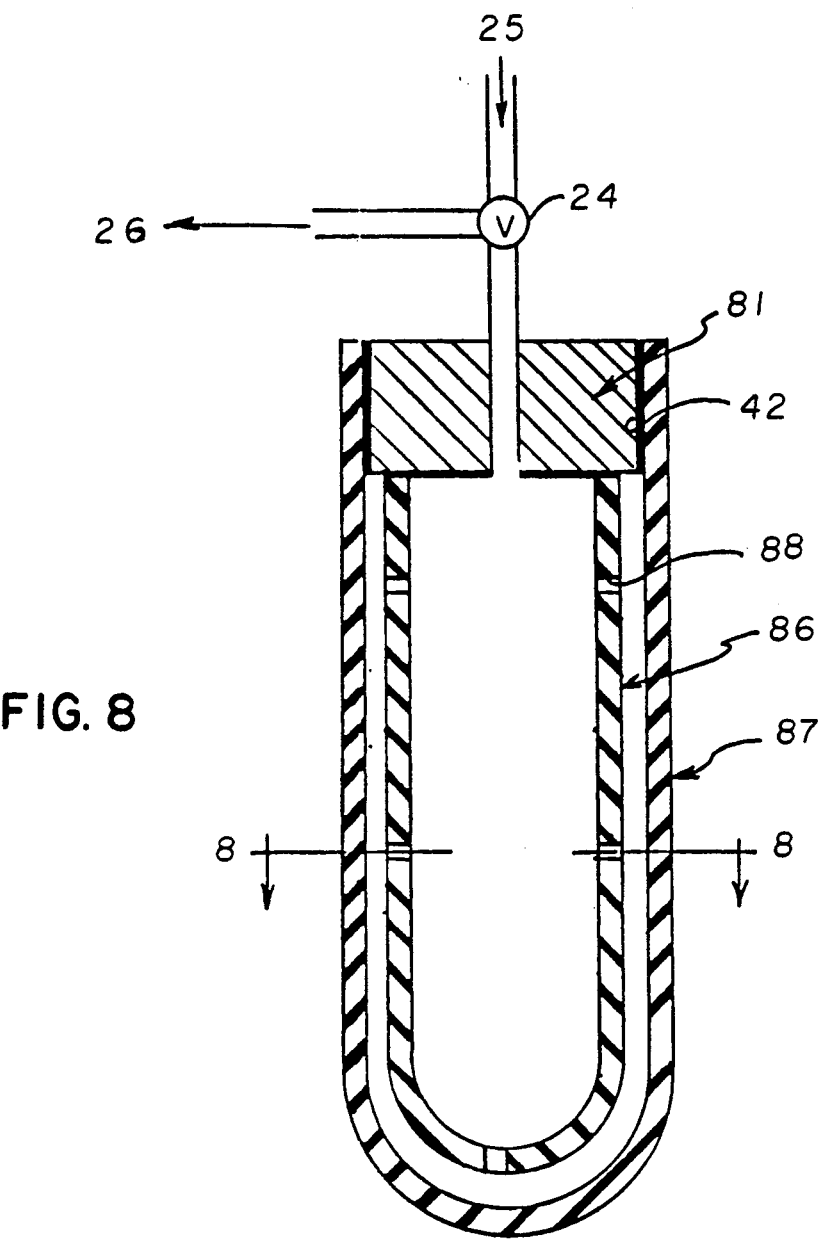
FIG. 8 is a longitudinal cross-section view of a test tube shaped UEM having a non-linear expandable envelope and a rigid, perforate core.

The embodiment shown in FIG. 8 is a modification of the embodiment shown in FIG. 6. This embodiment additionally provides a rigid core 86, rigidly connected to the mounting block 81 of the UEM. The rigid core 86 is surrounded by the non-linear envelope 87 (which may be uniform in wall thickness or profiled). The core 86 is shown as a perforate test tube form, having openings (perforations) 88. The core can be made of metal or rigid plastic, and its purpose is to provide additional mechanical stiffness to the UEM, which is an advantageous property of the mold, in particular with the dipping process, preferably, the envolope 87, in its relaxed state, fits snugly over and conformally to the core 86.

Figure 8A:
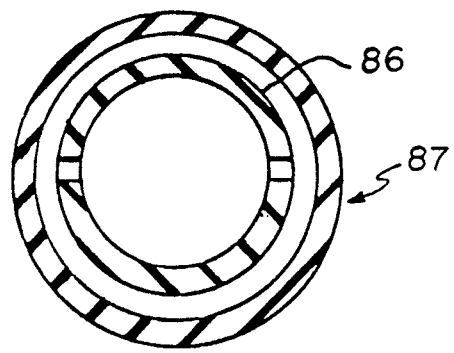
FIG. 8a is a cross-section of FIG. 8 along line 8-8.

FIG. 8a is a cross-section of FIG. 8 along line 8-8. In FIG. 8a the UEM of this embodiment is comprised (proceeding from the outside of the mold to its inside) of a non-linear envelope 87 and a core 86.

In the previous embodiments, the UEM envelope essentially expands in an unrestrained fashion, as the only forces acting on the envelope are its elastic forces and the forces exerted by the pressure differentials established (pneumatically or hydraulically) between the interior of the envelope and the atmosphere. In the following embodiments, two different restraining elements are introduced in the construction of a UEM, namely a liner and foam rubber.

Figure 11:
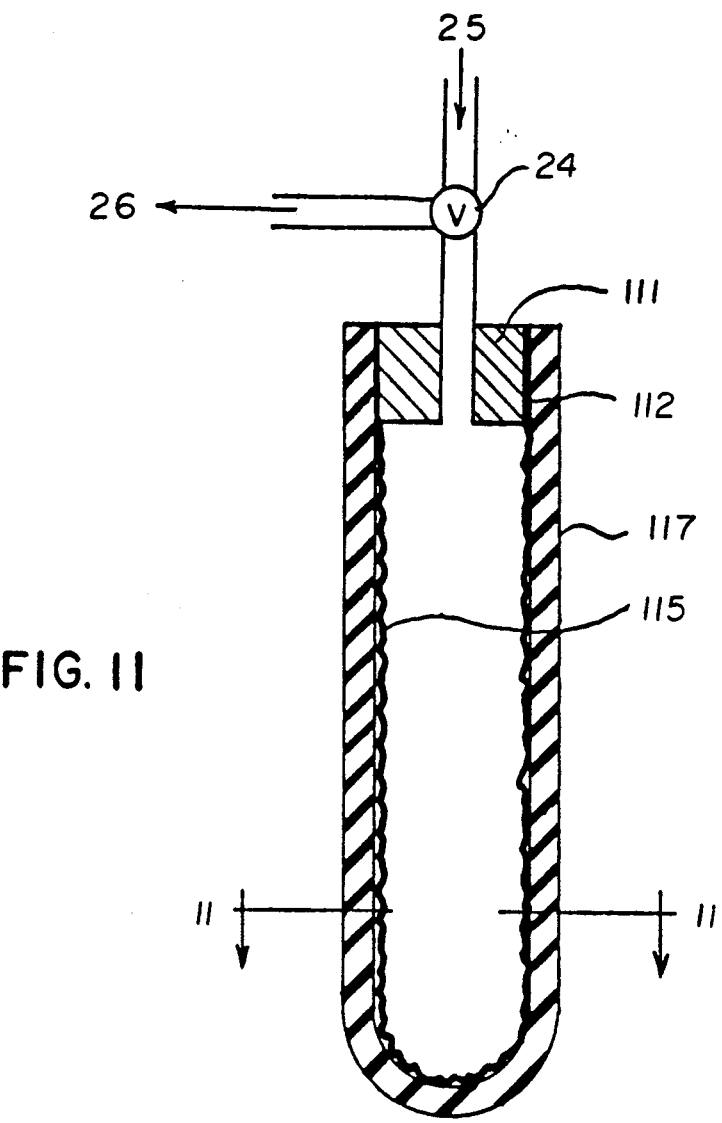
FIG. 11 is a longitudinal cross-sectional view of an embodiment of a test tube shaped UEM which includes a liner illustrated with the liner in its relaxed, unexpandable state.

In the embodiment shown in FIG. 11, the UEM has an additional element, a liner 115, in contact with the interior surface of envelope 117. Liner 115 is a thin, very flexible, but non-extensible "inner tube" so to speak, to the envelope 117. The liner 115 is made of any suitable plastic such as acetate, polyethylene and polypropylene. The liner can be cast or be formed on a rigid mold by well known techniquest, to the desired shape and size of the UEM in its expanded state.

Figure 12:
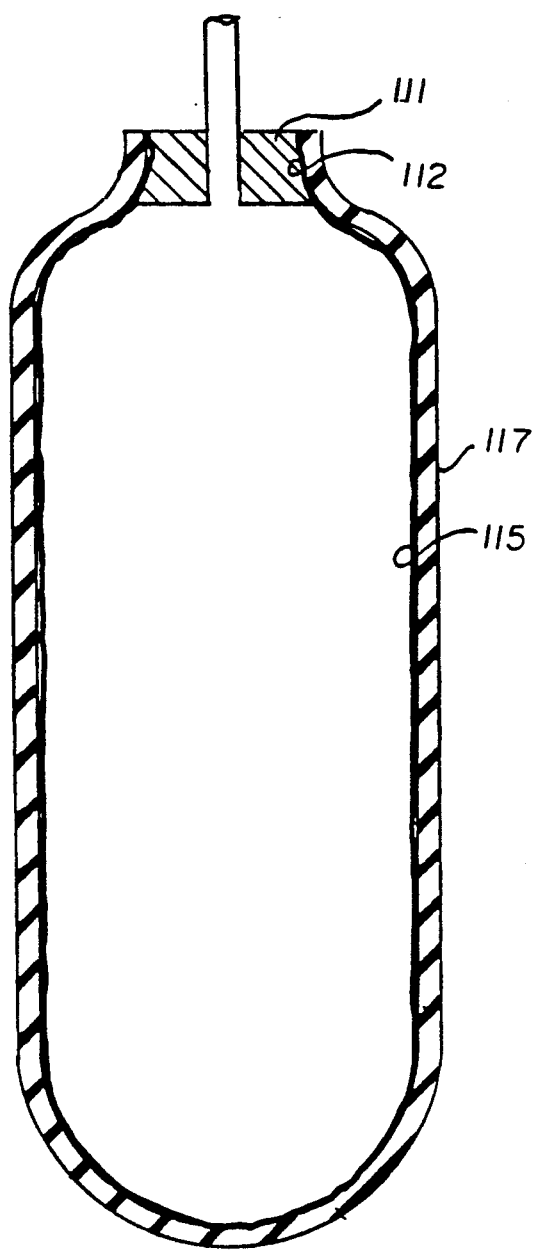
FIG. 12 is a longitudinal cross-section of a test tube shaped UEM having its liner and envelope in fully expanded state.

The liner 115 is made in a predetermined larger size and shape, and in order to fit the inside surface of the similarly shaped but smaller size envelope, the liner assumes a "wrinkled" shape, as shown schematically in FIG. 11. The air between the envelope 117 and the liner 115 is evacuated, and both are glued around and onto block 112 of the UEM, in glued area 112. Thus, as the hollow interior of the UEM is pressurized, the liner expands pushing the envelope 117 which elatically conforms to the expanding liner. The point at which the liner is smooth and taut and cannot expand beyond its predetermined size and shape, coincides with the final shape and size to which the UEm can expand. This is shown schematically in FIG. 12. On deflation, the elasticity of the expanded envelope contracts the liner along with it into a "crumpled" shape.

Liner 115, alternatively, can be made integral with envelope 117 by having the envelope stretch-coated, while the envelope is expanded to the desirable size and shape, with a liquid plastic, eg. cellulose triacetate in acetone solution. For example, one apparatus by which the stretch-coating can be performed is the embodiment of this invention shown in FIG. 15.

In other words, in this UEM embodiment the liner becomes integral with the envelope by stretch-coating the liner onto the envelope. Alternatively, the liner can be made from a thin, woven or nonwoven fabric in the shape of the envelope but of proportionally larger size. It is embedded in the elastic material of the envelope between the inner and outer walls. In this way, the embedded fabric liner limits the elastic expansion of the envelope to the size and shape of the fabric liner.

Figure 11A:
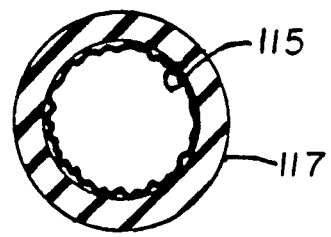
FIG. 11a is a cross-section of FIG. 11 along line 11-11.

FIG. 11a is a cross section of FIG. 11 along line 11-11. In FIG. 11a the UEM of this embodiment is comprised (proceeding from the outside of the UEM to its interior) of an (elastic) envelope 117 and a liner 115.

Figure 13:
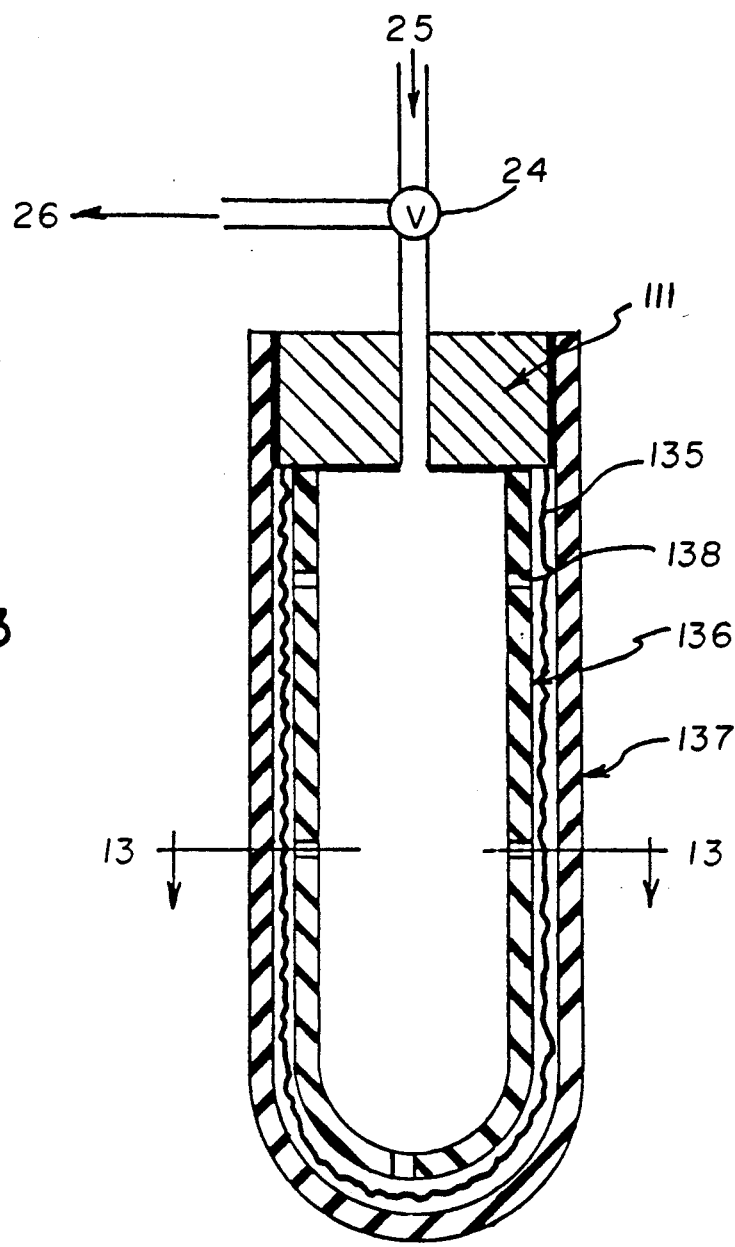
FIG. 13 is a longitudinal cross-section of a test tube shaped UEM having an expandable envelope and a liner in their relaxed, unexpanded state, and a rigid perforate core.
Figure 13A:
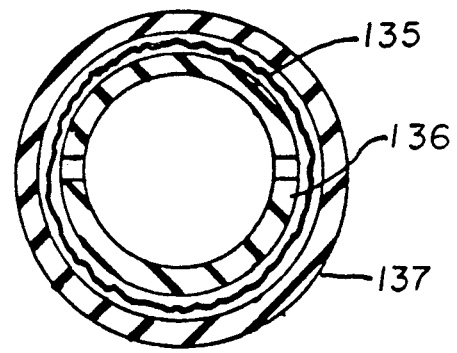
FIG. 13a is a cross-section of FIG. 13 along line 13-13.

The embodiment shown in FIG. 13 and 13a is a modification of the embodiment shown in FIG. 11. This embodiment additionally provides a rigid, perforate core 136, for providing additional mechanical stiffness to the UEM.

FIG. 13a is a cross section of FIG. 13 along line 13-13. In FIG. 13a the UEM of this embodiment is comprised (proceeding from the outside of the UEM to its interior) of an envelope 137, a liner 135, and a core 136.

Figure 5:
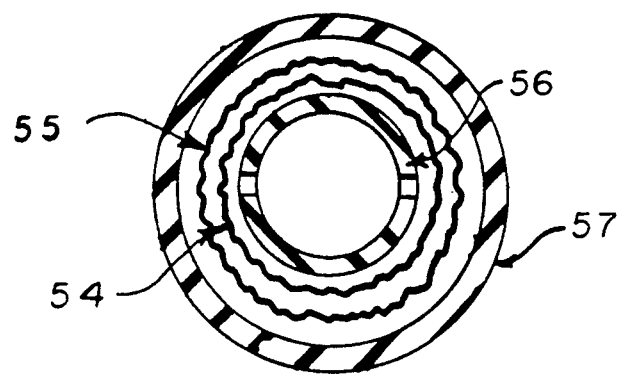
FIG. 5 is a cross-section view of a multistage expansion UEM having two liners, one inside the other.

A UEM can be constructed with more than one successive liners, in tandem, for multistage expansion of the mold. Thus FIG. 5 shows a UEM having two liners, 55 and 54. When the space between core 56 and liner 54 is pressurized (not shown) at a pressure $P_1$, the envelope 57 and liner 54 expand to the limits determined by 54. When additionally the space between 54 and 55 is pressurized (not shown) at pressure $P_2$, then the envelope 57 expands by an additional (fixed) amount, determined by the size and shape of 55. Multistage expansion UEMs can be used to perform progressive self-healing stretch-coating as described herein.

When a UEM employing a liner is used to stretch only a finished device, the envelope 57 may be omitted, leaving the UEM comprised of a core 56 and a liner 55.

Figure 15:
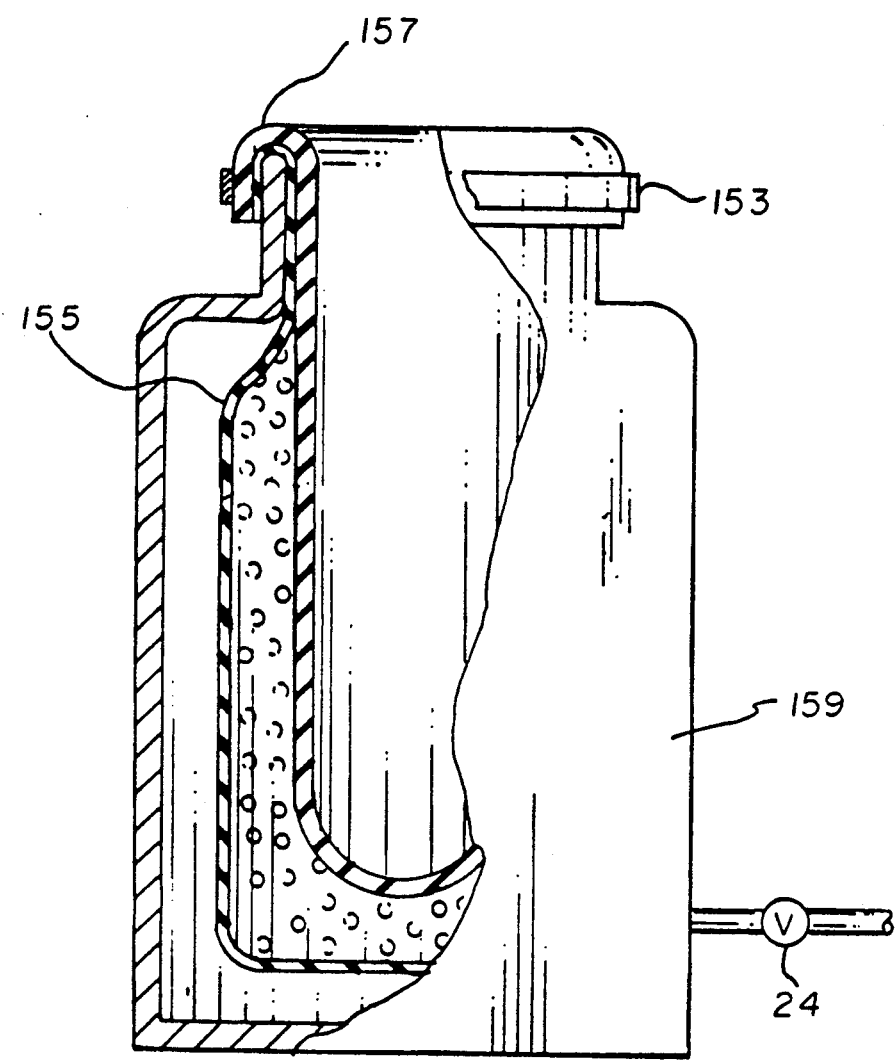
FIG. 15 is a cut-away longitudinal view of a vacuum UEM having a perforate liner and an expandable envelope.

In the embodiment shown in FIG. 15, a liner is used in a vacuum UEM in order to stretch-coat a finished elastic device from the inside. A perforate liner 155 is permanently installed in the vacuum chamber 159 as shown, by gluing the liner's open end around the neck of the chamber. An elastic device or envelope 157 is temporarily fastened around the vacuum chamber's rim by a mechanical fastening ring. Upon evacuation of the air in the chamber, the envelope 157 is drawn and stretched against the perforate liner 155, to a predetermined extent of shape and size determined by the non-extensible liner 155. At that stretched state, the elastic envelope 157 can be coated through the open end of the vacuum chamber with a liquid elastomer or plastic. The coating technique used may be spraying, for example, or "slosh" coating of the interior of the envelope 157.

The perforate liner 155 may alternatively be made of a rigid material. It may be a hollow form of any desired shape or size over which a finished elastic device (cf. envelope 157) can be conformally stretched for stretch coating.

In another variation, the thin, flexible, non-extensible liner 155 may be devoid of perforations. In this case, the air between the liner and the finished elastic envelope to be stretched is evacuated before the envelope is fastened around the rim. Upon establishing a vacuum in the chamber, the UEM behaves as in the embodiment of FIG. 15, stretching the elastic envelope against and conformally to the imperforate liner.

In the following embodiments described herein below, use is made of the agency (element) of open-cell foam rubber as the restraining element to the expansion of the elastic envelope E of the UEM, so that the envelope expands to a predetermined size and shape upon inflation of the UEM.

An arbitrary three-dimensional form cast of foam rubber has the property of being easily compressed, while it presents much greater resistance to deformations that tend to increase its volume, making the form practically non-extensible along any of its dimensions.

A polyurethane foam toy ball or a piece of foam rubber used in furniture cushions exhibits these properties of compressability without expandability.

Figure 9:
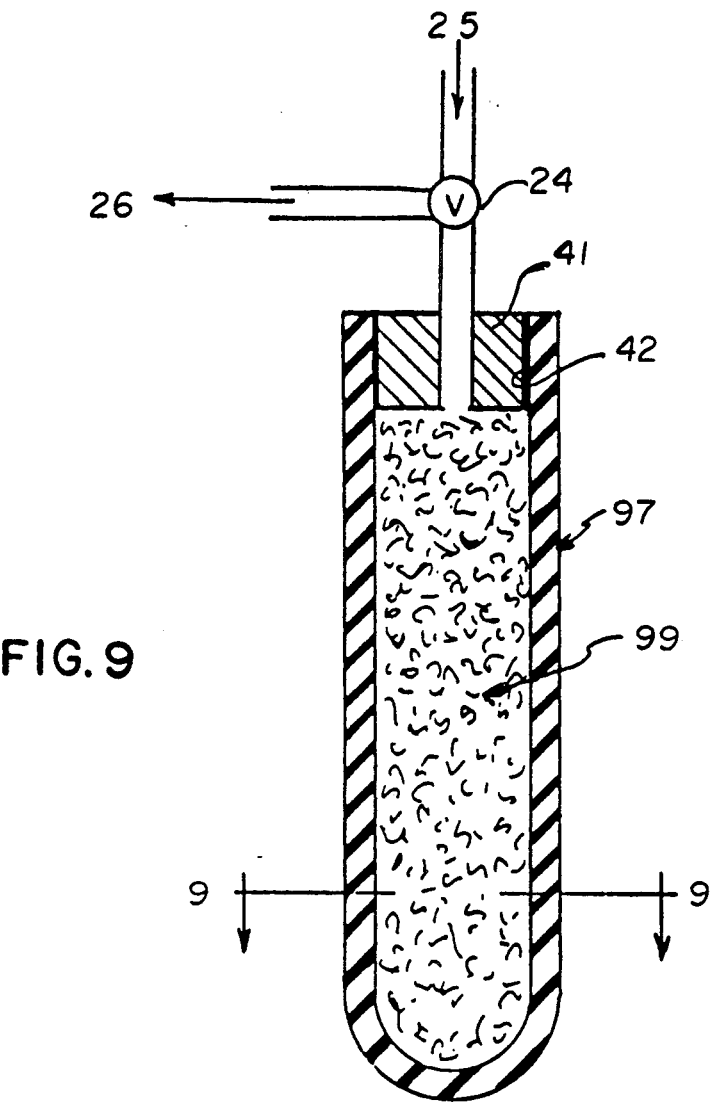
FIG. 9 is a longitudinal cross-section view of a test tube shaped UEM whose cavity, formed by an expandable envelope, is filled with open cell foam rubber.

In the embodiment shown in FIG. 9 the cavity formed by the elastic (rubber) envelope 97 is filled with open-cell foam rubber 99. The envelope is sealed to the foam in its entire inner surface in contact with the foam, so that the envelope becomes an integral "skin" to the foam. A suitable sealant is Dow Corning silicone rubber sealant 734. The foam rubber body 99 shown in FIG. 9 is under compression due exclusively to the elastic forces of envelope 97. The UEM in this embodiment is constructed as follows: First, the foam rubber is separately cast in the size and shape of the UEM in its expanded state. Then the envelope is sealingly fitted over the foam rubber shape, which easily compresses and assumes, practically, the size and shape of the elastic envelope surrounding it. The envelope/foam structure is then assembled into a UEM as in previous embodiments, as shown in FIG. 9. Alternatively, the elastic envelope 97 is stretched in the vacuum UEM described earlier in connection with FIG. 15, and it is filled with open-cell foam rubber. after vulcanization, the envelope/foam rubber structure is assembled in a UEM. A suitable open-cell foam rubber is Down Corning silicone RTV foam 3-6548. Additionally, this foam material sealingly adheres to the rubber walls of the UEM envelope, obviating the need for a sealant, as discussed earlier.

Figure 14:
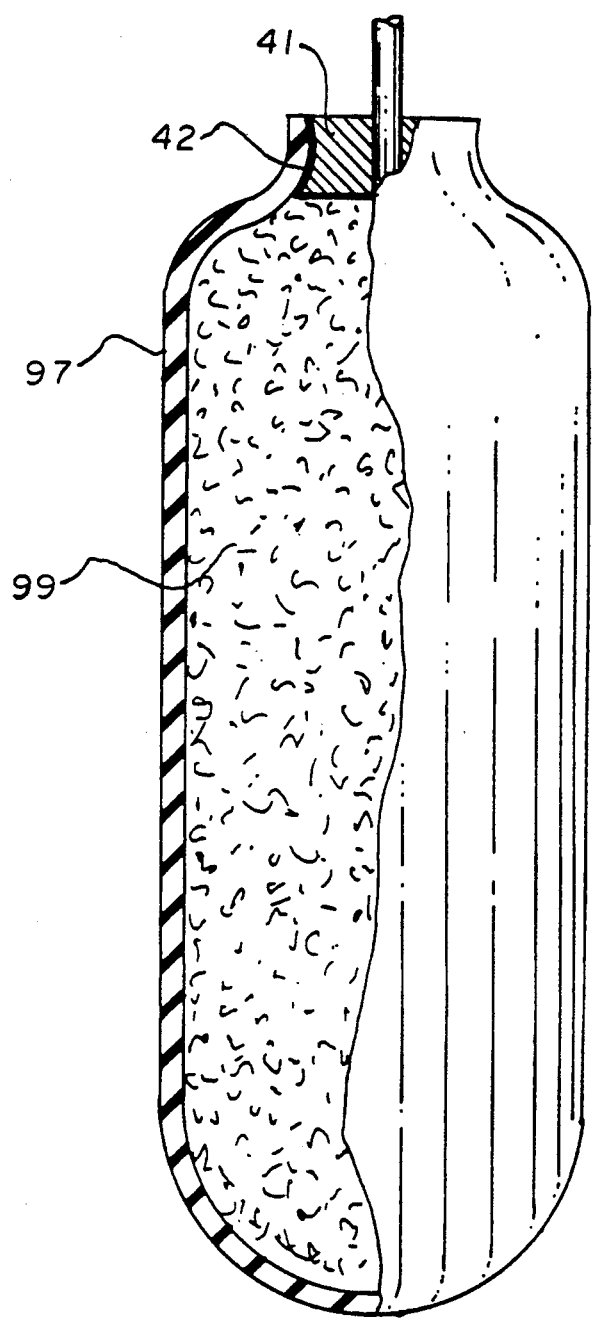
FIG. 14 is a cut-away view of a test tube shaped UEM, having an envelope filled with foam rubber in the fully expanded state.

FIG. 14 shows the UEM embodiment of FIG. 9 in its fully expanded state. Upon deflation, the elastic envelope 97 returns to its relaxed (unstretched) state, compressing in the process the rubber foam 99, as discussed earlier and as shown in FIG. 9.

Figure 9A:
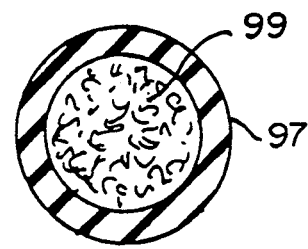
FIG. 9a is a cross-section of FIG. 9 along line 9-9.

FIG. 9a is a cross-section of FIG. 9 along line 9-9. In FIG. 9a the UEM of this embodiment is comprised (proceeding from the outside of the UEM to its interior) of an elastic envelope 97 and open cell foam rubber 99.

Figure 10:
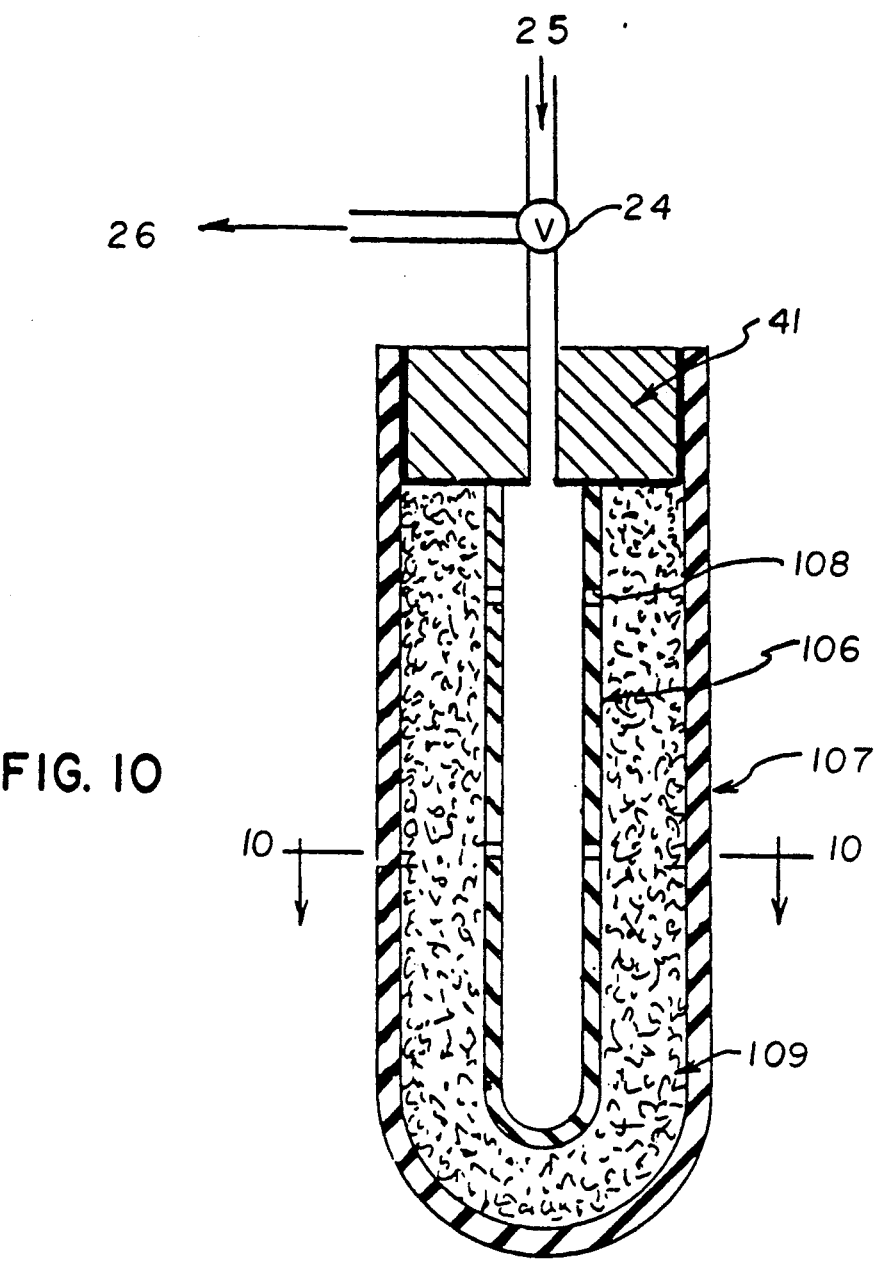
FIG. 10 is a longitudinal cross-section view of a test tube shaped UEM, having a rigid, perforate core, and the space between the core and the expandable envelope is filled with open cell foam rubber.

The embodiment shown in FIG. 10 is a modification of the embodiment shown in FIG. 9. This embodiment additionally provides a rigid, perforate core 106, for conferring additional mechanical stiffness to the UEM. The foam rubber 109 is also sealed to the perforate core 106.

Figure 10A:
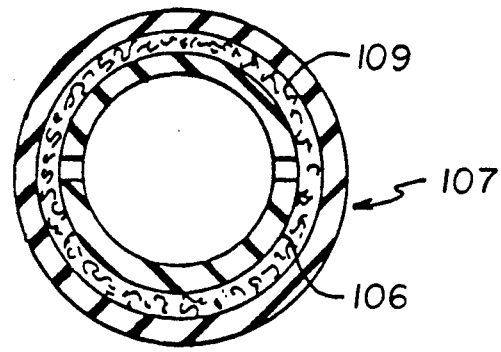
FIG. 10a is a cross-section of FIG. 10 along line 10-10.

FIG. 10a is a cross-section of FIG. 10 along line 10-10. In FIG. 10a the UEM of this embodiment is comprised (proceeding from the outside of the UEM to its interior) of an elastic envelope 107, open-cell foam 109 and a rigid core 106.

Additional useful embodiments of UEMs are constructed as follows: (107, 115, 109), (107, 115, 109, 106), (115, 109), (115, 106).

As a general remark, all of the above described UEM embodiments having the envelope element can be used for forming elastic articles or devices, process them with a minimum of manufacturing defects, for "stretch-washing" the elastic article to facilitate removal of solubles, stretch-coating them to render them "self-healing" and electrically testing them on-line in their expanded state. (Electrical testing requires that the UEM outside envelope surface is electrically conductive, by stretch-coating the envelope with a metal). These UEMs are particularly suitable for latex articles and devices manufactured by the "dipping" technique. On the other hand, all UEM embodiments devoid of an envelope element can be used only with finished elastic articles and devices. UEM embodiments utilizing a vacuum for expansion are used for stretch-coating the hollow (inside) surface of the mold of device.

UEMs are the essential apparatus for implementing the methods described herein to produce superior latex articles and devices.

An important feature of the methods described herein is "Shrink-mending". Devices such as medical gloves and prophylactics are predominately made of natural rubber latex by the dipping process. Some surgeons' gloves are made of natural rubber solution also by the same process.

Microporosity, pinholes and thin spots constitute the most common defects created in such devices during manufacture. The "shrink-mending", which is inherent in the methods of the present invention, eliminate the occurrence of such defects.

The method requires the use of a UEM in the appropriate form (of a glove or a test tube shape), over which the elastic membrane of the device forms, and according to the following steps:

(a) the UEM is expanded (pneumatically, hydraulically);
(b) the expanded UEM is dipped into a latex suspension;
(d) the UEM covered with the still wet, uncured layer of latex is permitted to return to its normal, unexpanded size;
(e) the wet, uncured "shrunk" latex layer is then cured on the UEM to form a latex device of a predetermined desired shape and size.

By reducing the area of the expanded latex coated UEM to a smaller size, the wet, uncured (partially "dried" or semi-cured) layer of latex is "squeezed" together during contraction of the UEM to fill-in and "mend" microporosity and any minute voids or thin spots formed in the latex layer, or any minute sites that could be potential "seeds" for such defects. Such localized voids and imperfections are created due to surface tension phenomena at the mold/latex interface, and/or localized inhomogeneities and/or impurities in the wet, uncured latex layer itself. If they are not "mended" while the latex layer is still uncured, they will remain in the latex to become microporosities, pinholes and thin spots in the cured (vulcanized) elastic membrane. Variations of the basic method outlined, include:

(aa) expansion of the UEM takes place while the mold is immersed in the latex suspension;
(bb) subjecting the immersed UEM to one or more cycles of expansion/contraction, the final state in which the mold is taken out of the latex suspension, being the expanded state;
(cc) introduce partial drying/curing in the process before a dip-coating step. In other words, a semi-cured latex layer is formed on the expanded UEM, dipped into the latex suspension, then the UEM is reduced to its normal, unexpanded size and then the latex layer is cured thereon;
(dd) a UEM is dip-coated in its relaxed, unexpanded state, it is then withdrawn from the latex suspension, the mold is expanded, and then it is dipped again and withdrawn from the suspension, finally it is reduced in size and the latex layer is cured;
(ee) gradually reducing the UEM to its normal, unexpanded size, while curing the latex layer on the mold. Under proper conditions, a "self-healing" latex device can be produced, by introducing mechanical stresses at the interface of the contiguous strata of the latex membrane being formed during this simultaneous curing and shrinking of the latex layer.

Additionally, tentative measurement data indicate that the final cured latex membrane produced by the shrink-mending method is denser (in specific density), than one produced by common dipping.

The advantages of the shrink-mending method are:
(i) it eliminates or drastically minimizes the occurrence of pinholes and thin spots, resulting in reduction in the rejection rates of finished latex devices;
(ii) the finished device has the properties of one made with a higher grade latex due to the slightly higher density of a latex device produced by this method;
(iii) the only change necessitated in a current production line is the substitution of the conventional rigid molds with UEMs.

Another important feature of the methods described herein is Post-cure "stretch-washing".

The FDA Medical alert of Mar. 29, 1991 and the letter dated May 1, 1991 addressed to all manufacturers of latex devices are incorporated herein by reference. They pertain to post cure processing and assert: "Depending on the nature of the latex device, manufacturing process and intended use, some latex devices may also need off-line washing with hot water after completion of the curing process. Also, surface treatment of the cured latex device with chlorine or other agents may denature surface constituents, such as water soluble proteins".

Experiments were performed in which medical gloves and prophylactics were immersed in boiling distilled water having in solution food-grade dyes for 10 minutes. The "dyed" latex devices were rinsed with distilled water to remove excess dye and then some of the devices were:
(a) soaked in hot distilled water for one hour;
(b) while an equal number of devices were stretched by means of a UEM and spray-washed with hot distilled water—a process referenced herein as "stretch-washing"—for five (5) minutes.

It turned out that the stretch-washing treatment removed much more dye than soaking in water.

Extrapolating from this preliminary simulation to the manufacturing domain, stretch-washing should also be effective in removing of solubles in post cure washing of latex devices.

When such latex devices were halogenated in a chlorine bleach solution, while stretched on a UEM—a process referred to herein as "stretch-halogenation" and "surface stretch processing"—the subjective evaluation by feel was preferable to that of the devices halogenated in their relaxed state. This is due to the larger halogenated area which shrinks back to the smaller surface area of the device in its relaxed state, thereby modifying its "feel".

The method of "stretching processing" may also have additional applications to post cure processing of latex devices, such as treating a finished device with an anti-oxidant, for example, to extend the shelf life of the device; and for treating the surface of a latex device to render it hydrophilic.

Additionally, the stretch-halogenated devices exhibited a measure of the "self-healing" property observed in latex devices stretch coated with an elastomer.

Another important feature of the methods described herein is On-line electrical "stretch-testing".

A stretch metallized UEM can be made part of an electric circuit wherein the finished device, expanded on its UEM, is immersed in an electrolyte (e.g. a saline solution), and the ionic current through the entire device is monitored. In this way, the device is electrically tested while it is simultaneously stretched in three dimensions, thereby enlarging pinholes and other manufacturing defects, so that they become detectable in a device which may pass an electrical test in its unstretched state.

Another advantage of using a UEM for on-line stretch-testing is that all finished devices are tested, as contrasted with current testing methods wherein only a small statistical percentage of the finished devices is tested.

Another important feature of the methods described herein is stretch-coating.

A UEM is indispensable for stretch-coating shaped elastomeric devices with elastomers to render them "self-healing" and for stretch-metalizing elastic devices with a continuous or a discontinuous metal layer to render them electrically conductive or to form a pathogen impermeable barrier on the device. Examples of such devices follow as examples of the products produced by the molds and methods of the present invention.

Figure 16:
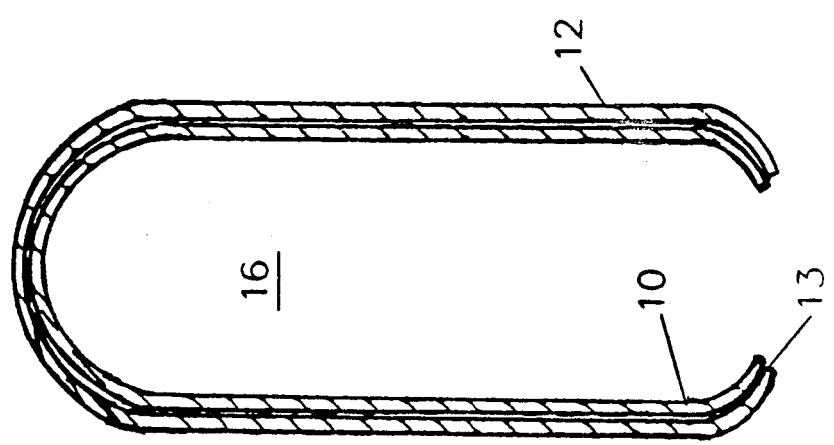
FIG. 16 is a cross sectional view of a thin rubber article that is stretch coated according to the present invention.

FIG. 16 illustrates a preferred embodiment of the invention wherein a thin base layer of natural latex rubber is linearly stretched two dimensionally which causes the article made therefrom to expand three dimensionally, and while maintained in this stretched condition, is uniformly coated with a thinner overlayer 12 of the same rubber material, or of silicone rubber, in such manner as to form an integral bonding of the two layers 10 and 12 at an interface area 13. The thinner overlayer 12 seals pinholes or other small openings in the base layer 10 when stretched, and thereby considerably improves the ability of the resulting laminate to resist the passage of fluids therethrough. The resulting multilayer rubber sheet, or shaped article, is also strengthened, as well as being made more imperforate than the single base layer 10 alone.

Figure 17:
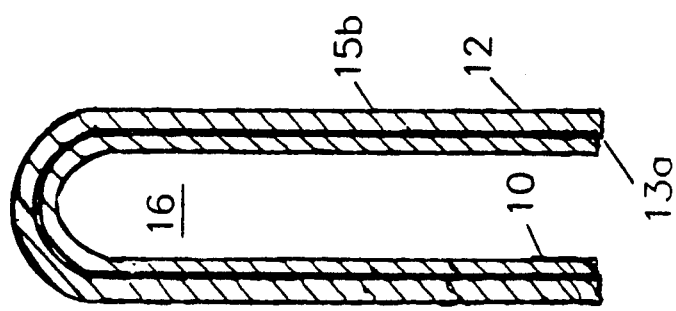
FIG. 17 is a cross sectional view illustrating the coated article of FIG. 16 in a relaxed state.

When the resulting article is permitted to elastically contract to a more relaxed state, as shown in FIG. 17, the thinner overlayer is compressively stressed, providing an observable fine wrinkling 15b at the outer surface of the overlayer 12, as shown. The contraction of the article is depicted in FIG. 17. At the interface region 13a, between the two layers 10 and 12, there is also provided a differentially stressed region, with the interacting portions of the overlayer 12 being maintained in compression whereas those of the base layer 10 are in tension.

Thereafter as the dual layer elastomeric article is progressively stretched outward to an extent less than when it was coated (as shown in FIG. 16), the wrinkling 15b at the outside surface of the outerlayer 12 is progressively diminished until returning to the condition shown in FIG. 16. This stretch coated elastomeric product has been found to exhibit two improved properties.

Initially, as discussed above, it has been found to be somewhat stronger and more resistant to the passage of fluids therethrough. The second improved property that has been found to exist in the stretch coated article is that of "self-healing" of the article against leakage, in the event that a small pinhole or opening is later formed in the article 16 after it has been stretch coated as described above. In fact, it has been found that the stretch-coating process of FIG. 16 also seals previously formed pinholes, or other very small opening in the base layer 10; and maintains this sealed condition despite repeated stretching and relaxing of the coated article 16, within a limit less than when the overlayer 12 was applied.

More specifically, it has been found that in the event that a small pinhole previously existed, or was later formed, in the stretch-coated article of FIG. 16, that the overlayer 12 seals such opening, and maintains this sealed condition despite repeated stretching and relaxing of the article 16 to an extent less than when it was coated. This self-healing function is believed to result from the compressive stress created in the overlayer 12, and in the interface area 13a between the two layers 10 and 12, as a result of the stretch-coating process. Tests have shown that this self-healing property has been found not to exist in ordinary laminated layers of rubber, when the base layer has not been stretched prior to coating with the overlayer. Such tests have demonstrated that in ordinary multiple layered rubber sheeting, a pinhole previously, or later formed in the article, has been found to leak when the thin rubber article is stretched, and that the leak persists with repeated stretching.

According to one preferred embodiment of the invention, the thin rubber base layer 10 of natural latex rubber is formed by any of the well known processes practised in the prior art, in a variety of different shapes and sizes, by dipping a shaped mold into a liquid latex solution, or otherwise coating the mold. The thickness of the resulting rubber layer is controlled by repeated dipping of the mold, to yield thicknesses in the range of about 0.005 to 0.0012 inches, that have been found most useful for many different products. The base layer can, of course, be formed in other thicknesses.

After curing, the base layer 10 is then stretched to a desired extent using an expandable mold (not shown), or applying the cured layer onto a larger mold to stretch the layer or shaped article to a desired extent. It has been found that the stretch coating process can be satisfactorily performed by stretching the base layer 10 or shaped article, over a range of from 10% greater to 100% greater, or even more, than in its unstretched, relaxed state.

The overlayer 12 is preferably of the same natural latex material, or of silicone rubber, and is applied and intimately adhered to the cured base layer 10, or shaped article thereof, by a similar one of the well known rubber forming processes, including dipping, spraying, or otherwise coating over the cured base 10. The overlayer 12 is preferably formed in thickness ranging from 10% of the thickness of the base layer 10 up to about ½ of the thickness of the base layer 10. A thin overlayer 12 is usually desired in order to maintain the thickness of the coated article close to that of the single base layer 10, and to approximate the degree of stiffness or elasticity close to that of the base layer 10 alone. It has been found that the elasticity of the resulting two layer rubber article made according to the present invention remains in the same range as that of the base layer alone. This is believed to result from the fact that the compressive stress resulting in the overlayer 12 (when relaxed) are in opposition to the tension stresses created in the base layer 10 by the process. Therefore an externally applied force in a direction to stretch the resulting article 16, is aided by the stresses in the overlayer 12.

Briefly recapitulating the steps of one preferred process according to the invention, a thin base layer 10 of natural latex rubber, or a shaped article formed thereof, is stretched over a range of 10% to 100% greater than the layer in its relaxed state. While maintained in this stretched state, a thin overlayer 12 of the same material, or of silicone rubber, is coated and intimately adhered to the base layer 10, in a thickness ranging from 10% to ½ of that of the base layer 10. The coating is cured and the article 16 subsequently removed from its mold and permitted to return to a relaxed state. The resulting article approximates the thickness and degree of elasticity of the single rubber layer alone, yet possesses the improved properties of greater strength and considerably improved resistance to leakage of fluids. Still further, the resulting article possesses a self-healing property that provides sealing of the article against leakage through preexisting pinholes, or those later formed, despite repeated stretching and relaxing of the article, or shaped product formed thereof.

EXAMPLE 1

A number of thin, latex rubber strips were obtained from standard, commercially available medical grade rubber products, and each was electrically tested for leakage in an electrolyte (saline solution) by detecting the passage of ions therethrough.

All of the strips were then stretched and the electrical tests for leakage were repeated. The tested rubber strips were then divided in three groups:

A. Strips that did not leak (no pinholes or small openings) either before or after stretching.

B. Strips that did not show leakage of ions when tested in their relaxed state but showed leakage when stretched and then tested.

C. Strips that leaked both during tests when relaxed and tests when stretched.

A fourth category was then created:

D. Some of the strips from the first group that did not leak when stretched or relaxed, were then pierced with the point of a small sewing needle.

Each above group A, B, C, and D, were then divided into first and second subgroups. The strips in all of the first subgroups were coated with rubber while in an unstretched state; and those in all of the second subgroups were first stretched and then similarly coated as in the first subgroup but while in their stretched state.

All coated strips were then electrically tested for leakage in an electrolyte, as described above, with the following results:

All strips in the first subgroup of Groups B,C, and D (those that were coated without being first stretched), were found to leak ions whenever the strips were even slightly stretched in the electrolyte. The leakage continued after such strips were then permitted to relax.

In contrast, all strips in the second subgroups of Groups B, C, and D (those that were stretch coated, as above described) did not leak when electrically tested despite repeated stretching and relaxing in the electrolyte. The degree of stretching was limited to that during coating of the base layers.

EXAMPLE 2

A similar series of thin rubber strips was obtained and each was stretched to a different extent (e.g. 15%, 20%, 25%, 35%, and 50%), and while so stretched was coated with a thinner overlayer of rubber as described above, and then cured.

The strips were electrically tested for leakage as above described; and all exhibited the self-healing property as described above when repeatedly stretched and relaxed during the leak testing. However, each strip was stretched only to the limit corresponding to that when it was coated.

EXAMPLE 3

A similar series of thin rubber strips was obtained and each was stretch coated while being stretched to the same extent as the others. However, each different strip was coated from a different dilution of silicone rubber in a solvent (e.g. by volume, 10%, 15%, 20%, 25%, 35%, and 50%), using Dow Corning #734 RTV sealant in Dow Corning Cyclomethicone.

The strips were electrically tested as described above, and all exhibited the self-healing property despite repeated stretching and relaxing of the strips during electrical testing (but within the limit of stretching corresponding to that when the strips were coated).

Figure 18:
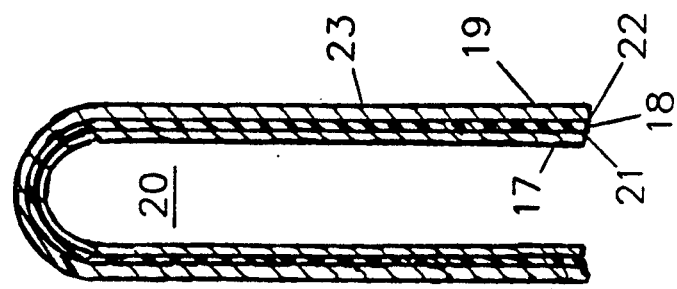
FIG. 18 is a cross sectional view illustrating an embodiment of the coated article which provides more than one overlayer of rubber.

In alternative processes as depicted in FIG. 18, a plurality of overlayers of rubber 18, and 19 are applied and integrally adhered to the stretched base layer 17, of rubber, to provide a three layer rubber article, or shaped product thereof. The overlayers 18 and 19 may be successively applied, and successively cured, each on top of the other, as shown, or may be applied on opposite sides of the base layer 17 (not shown).

The base layer 17 may be differently stretched during the coating of each different one of the overlayers 18 and 19 to impart a progressive self-healing property to the article. Thus, for example, the base layer may be stretched by 45% and the first overlayer 18 applied and cured. Thereafter the article may be stretched by 80% and the second overlayer 19 then applied over the first overlayer 18, and then cured or may be applied on the opposite side of base layer 17). Still additional thin overlayers may be applied on the same or opposite sides, or both, to still further modify the self-healing properties of the resulting article.

Various different kinds of rubber and related materials may be employed in practising the invention including natural latex rubbers, synthetic rubbers, silicone rubbers, polyurethanes, and other medical grade elastomeric copolymers. The thicknesses of the base layer, and the one or more overlayers, may also be varied to provide the necessary strength, elasticity, and/or stiffness of the resulting articles.

Surgical gloves are an obvious article to be manufactured using the UEM mold technique described above and an equally critical product which benefits from the invention is the condom or prophylactic.

Prophylactic devices for the prevention of sexual disease are usually made of natural rubber latex material in very thin wall thicknesses ranging from 0.03 millimeters (30 micrometers) to 0.07 millimeters (70 micrometers). Such very thin membranes of highly elastic natural materials have been found most desirable to minimize interference with active movement during use as well as permitting the users to retain the nerve sensations and experiences during such use.

However, natural rubber material, in such thin wall membranes, does not provide a continuous, impermeable barrier to the passage of micro-size pathogens, such as the virus causing AIDS or HERPES. Such virus are known to be as small as 0.1 micromillimeter micrometer (0.001 mm), or about 250 times smaller than the length of the human sperm and at least 30 times smaller than the thickness of such sperm. The natural rubber membrane is comprised of a polymer matrix characterized by myriads of randomly distributed microsize openings or pores formed among the polymer chains. Thus although such natural rubber prophylactics have been found to be an effective barrier preventing the transmission of the larger sperm, there is no assurance that such devices are effective in preventing the transmission of such much smaller virus, and some testing to date has indicated to the contrary.

Additionally, the elastic membrane is cyclically stretched and relaxed in three dimensions during its intended use, resulting in repeated stressing of the membrane and reductions in its wall thickness, during such use. This action is believed to result in repeatedly enlarging and reducing the micro-size openings in the membrane, thereby increasing the probability of pathogens passing through the membrane.

Despite extensive quality control testing of the prophylactics during manufacture, the membranes are not manufactured with absolutely uniform wall thicknesses, whereby during use different areas of the walls are not uniformly stressed nor uniformly stretched, resulting in "weaker spots" or areas and occasional bursting under severe stressing. The International Planned Parenthood Federation estimates that even from the best manufacturers, the prophylactics have a bursting rate during use of 0.1% whereas those from the worst manufactured brands have a burst rate as high as 1%. Similar statistical data is not yet available, or has been published, with respect to the effectiveness of rubber prophylactics in preventing the transmission of virus, such as those causing AIDS and HERPES. It is widely believed, however, that presently available prophylactics are not very effective in preventing the transmission of such sexually transmitted diseases.

It has been found that a substantially continuous thin, ductile metal coating or layer may be provided over the surface of the prophylactic device, without fracture or breaking despite repeated stretching and relaxing of the device such as would occur during intended use. This is accomplished by forming the metal layer in such fashion that it can be repeatedly expanded and contracted, with the elastic membrane, without fracturing or breaking of the thin metal layer. According to one preferred manufacturing process, the elastic membrane is initially stretched to the extent of its intended use, and a continuous coating of highly ductile metal is thinly applied to the stretched membrane to seal its surface. In another process, the stretched membrane is initially thinly coated with an additional elastic material, and the resulting coated device permitted to again relax, forming a pattern of wrinkles on its surface. The thin ductile metal seal is thereafter applied to the wrinkled surface, thereby to form a correspondingly wrinkled metal layer that can be expanded and contracted without fracture or breaking. In still a third process, the surface of the membrane is embossed or patterned, in a similar configuration of undulations or wrinkles, and is then continuously coated with a thin layer of highly ductile metal, thereby to provide an expandable metal seal.

The micropore openings that are formed in conventionally manufactured prophylactic articles, of natural latex rubber and other elastic materials, can be sealed by a continuous, thin film, coating, or layer of a ductile metal, such as aluminum; and that such a seal can be maintained despite repeated stretching and relaxing of the elastic article without fracturing or cracking the thin metal layer. This is performed by using a highly ductile metal for the layer and by forming the layer with undulations, folds, or wrinkles in its thickness, such that the metal layer can be expanded and contracted to progressively smoothen the folds and restore the folds, without fracture or breaking of the metal seal.

In one preferred UEM process of manufacture, a conventional prophylactic article of natural latex rubber is prestretched on a mold such as that illustrated in FIG. 2 for example, to the extent expected during use. It is then coated with substantially pure aluminum, in a vacuum deposition chamber, to form a thin, continuous film of aluminum directly onto the surface of the rubber article. In a preferred embodiment, the UEM mold is relaxed when coated with the latex and expanded by the differential pressure which is controlled by value "v" but created by the vacuum of the deposition chamber. The coating process is continued to form a metal film having a thickness ranging from 500 Angstroms to 1500 Angstroms.

To insure that the deposited metal layer properly adheres to the stretched elastic article, the surface of the rubber is carefully cleaned by chemical solvents, and/or by other cleaning methods either mechanical or electrical, prior to metalizing the surface.

Upon completion of the coating process, the metalized article is removed from the vacuum chamber, and from its expansion mold, and permitted to relax to the normal relaxed size of the article.

EXAMPLE 4

A prophylactic article of standard commercial manufacture was stretched in a mold in two dimensions to twice its normal length and thickness (100%). Its outside surface was then cleaned of contaminants by being swabbed with isopropyl alcohol. The mold was then placed in a CYC thermal evaporator of conventional commercial design, and vacuum metallized at a vacuum of about 10 TORR. The ductile metal used for coating was 99.7% pure aluminum, and this metal was resistance fired in the evaporator for a period of about (7) seven seconds. To obtain a more uniform coating on the article, the mold was supported on a revolving rack "cluster" inside of the evaporator, and revolved about five (5) times during a seven (7) second coating interval.

After receiving the metal coating, the article was removed from the evaporator, and from its expansion mold, and permitted to resume its relaxed elastic state. It was then subjected to various tests, including an electrical conductivity test, and various observation tests under a 50 power microscope. These tests initially confirmed the continuity of the metal film over the article. The coated article was then subjected to repeated cycles of stretching and relaxation, within the 100% limit of its coating, while under microscopic examination. These tests revealed the undulated, wrinkled, or folded, surface configuration of the metal layer when the article was disposed in a relaxed state, and the progressive smoothing of the metal undulations, wrinkles, and folds as the elastic article was stretched. No fracturing, cracking, or breaking of the aluminum film was observed under the microscope during the repeated cyclical stretching and relaxing of the elastic article. The electrical conductivity tests also did not reveal any breaks in the electrical conductivity of the aluminum film during the repeated stretching and relaxing of the article.

EXAMPLE 5

A prophylactic article of standard commercial manufacture was stretched on a mold in three dimensions to one half greater (50%) than its normal length and diameter, and aluminum metallized in a vacuum evaporator in the same manner as in EXAMPLE 1, above.

The same tests as in EXAMPLE 1, were conducted, but the cyclically repeated stretching and relaxing of the metalized article were limited to an extent only 50% greater than the relaxed length and diameter of the article. The test results were the same as found in EXAMPLE 1.

EXAMPLE 6

The same process as in EXAMPLES 1 and 2 was conducted but the prophylactic was prestretched only 10% greater in size than in its relaxed state.

The resulting article was tested in the same manner as in EXAMPLES 1 and 2, but was stretched during testing by only up to 10% greater than in its relaxed state.

The test results were the same as found in EXAMPLES 4 and 5.

EXAMPLE 7

The same metallizing process of EXAMPLES 4, 5, and 6 was performed using a standard, commercially available prophylactic article, but the elastic article was not prestretched during the metallizing of its surface with aluminum. Instead the article was placed on a non-expansion mold and accordingly metal coated while in its relaxed state.

The resulting product was tested in the same manner as in EXAMPLES 4, 5, and 6 above; including cyclically stretching and relaxing the article while microscopically observing the metal surface, and electrically testing the metal surface.

The stretching of this article produced fractures, cracks, and crazing in the metal film layer that were observable under the microscope.

EXAMPLE 8

The metallized article samples in EXAMPLES 4, 5, and 6 were each subjected to additional cycles of repeated stretching and relaxing but were expanded during stretching to a degree beyond the limit of their prestretching during the metallizing processes.

In all examples, when the articles were expanded beyond their prestretched limits during coating, the tests revealed fracturing, cracking, and crazing of the aluminum film.

For the samples of EXAMPLE 4: Cracks were found when expanded beyond 100% of the articles relaxed size.

For the samples of EXAMPLE 5: Cracks were found when expanded beyond 50%.

For the samples of EXAMPLE 6: Cracks were found when expanded beyond 10%.

For the samples of EXAMPLE 7: Cracks were found for any expansion.

EXAMPLE 9

A series of additional prophylactic articles of standard commercial manufacture were metallized with aluminum using the same process as described above, in EXAMPLES 4, 5, and 6. However, the aluminum layers were coated to twice the thickness as in these examples e.g. 1000 Angstroms to 1500 Angstroms.

Each of these metalized articles were tested in the same manner as the corresponding one in the above EXAMPLES. The test results were found to be the same for the thicker aluminum films or layers than for the thinner aluminum layers.

In addition to aluminum, a number of other ductile metals may be used to provide the very thin metal seal over the article, including gold, silver, platinum, and other metals, including metal alloys. All of these very ductile metals can be applied in very thin coatings to the elastomeric surface of the article by a vacuum vaporization process, as described, or by other known processes for coating metals, including metal sputtering and electroless plating. Such otherplating methods may be more useful where the article is made from other substrate materials, other than natural latex rubber, where such other materials cannot be plated by metal vaporization.

Alternatively, the metal film seal may be provided by plating a series of ductile metal films to the surface, instead of a single coating. Each of the different layers may be of the same metal, or of different ductile metals, and with each layer being applied successively over the previous layer.

It has been found that a minimum thickness of the metal must be coated to insure obtaining a continuous metal sealing of the surface of the article. This minimum thickness of the metal film depends upon a number of parameters, including the ductile metal being used, the process of forming the metal film, and the substrate material used in the prophylactic article. Although natural rubber latex is the most widely used material for such articles, a number of other materials are in lesser use, including polyurethane and others. It has also been found that the plated thickness of this metal film can exceed the minimum thickness by about one order of magnitude, as shown by the ADDITIONAL EXAMPLES, discussed above, without impairing the performance of the metal seal or barrier, despite repeated stretching and relaxing of the article.

For the purpose of protecting the thin metal layer against abrasion, thin film of suitable lubricant, such as silicone oil, may be later applied over the metal coating. Alternatively, the metal film can be overcoated with a very thin layer of the same elastomeric material, as is used in the article, or other suitable elastomeric material can be used. This thin protective overlayer is applied over the metal film while the article is still on its stretching mold. In this manner, the elastomeric overlayer conforms to the undulations, wrinkles, and folds in the metal film that are formed when the article is removed from the mold and elastically contracted to its relaxed state.

A number of alternative UEM processes for making the improved article may be used. The prophylactic article may be prestretched, as before, to an extent expected during use, and the expanded article can be precoated with a thin intermediate layer of the same elastomeric material, such as natural latex rubber. This precoating of the stretched article with an elastomer may be performed in the same manner, by dip-coating, as is usually used in the manufacture of such articles.

After precoating, the article is removed from its stretching mold and permitted to elastically contract to its relaxed state. The shrinking of the article correspondingly shrinks the intermediate elastomeric layer, producing undulations, wrinkles, and folds in the surface of the intermediate layer as the article is relaxed. The wrinkled intermediate layer is then metalized or coated with a thin layer of aluminum, or other ductile metal, to provide a continuous metal covering and seal, covering the undulations, wrinkles, and folds in the intermediate layer.

In the same manner as discussed above, the resulting metallized article can be repeatedly stretched and relaxed, within the limit of the original stretching, without fracture, cracking, or breaking of the metal sealing film. Stretching of the article tends to progressively smooth the undulations, folds, and wrinkles in both the intermediate layer and in the correspondingly undulated metal layer, without destroying the integrity of the metal seal or barrier.

According to a still further process of making the improved article, the outer surface of the elastomeric article is patterned to provide undulations in its outer surface, including a pattern of wrinkles or folds, thereby to increase its surface area. This can be performed by mechanical abrasion, or by chemical etching, or by optical or electrical cutting means, including a laser beam or an electron beam, respectively. This patterning of its surface is performed while the article is disposed on a mold and maintained in its relaxed state. A thin coating or film of ductile metal, such as aluminum, is then applied over the undulated surface, following and sealing the undulations, folds, and wrinkles in a continuous covering. The metal film is applied by vapor deposition under a vacuum, as previously described, or by metal sputtering, or electroless deposition. In the same manner as previously described, the resulting metallized article can be repeatedly stretched and relaxed without fracture, cracking, or breaking of the thin ductile metal layer. Instead, stretching of the article, within the limits imposed by the patterned surface, results in ductile expanding the outer metal layer, smoothing the undulation, wrinkles, and folds in the metal film.

It will be appreciated by those skilled in the art, that the size and number of the undulations, wrinkles, and folds formed in the ductile layer determines the extent that the metal film can be expanded while maintaining its structural integrity. The elastomer prophylactic member is also initially made thicker than usual to provide the necessary strength without tearing when the article is repeatedly stretched.

The products created by this invention are enhanced by the formation of a reticulated interface. For a reticulated surface to form, the elastomeric material of the thinner (elastomeric) coating must be of a higher modulus of elasticity than that of the material of the base membrane.

Accordingly, a reticulated surface will not form on a membrane "stretch-coated" with the same unmodified, base material of which the membrane is made.

For example, a membrane of a particular RTV silicone rubber (these types of elastomers are easy to work with), when stretch-coated with a thinner overcoat of the same material that the membrane is made of, it does not form a reticulated surface under any combination of degree of stretching and thickness of the overcoat. In the same example, however, when the liquid silicone rubber used for the thinner overcoat is loaded with an inert filler such as fumed silica or carbon black, a reticulated surface forms readily. The explanation is that the addition of these powders to the silicone rubber increases its modulus of elasticity—the rubber becomes "stiffer".

The principle on which the first two alternative processes are based is that a reticulated surface is first formed on a prophylactic article and then the reticulated surface is metallized in its relaxed state, to form a stretchable film.

In addition to incorporating filler materials in an elastomer to change to a varying degree its modulus of elasticity, the modulus of elasticity can be also formulated for an elastomer by means of:

(a) varying the degree of cross-linking of the elastomer; and/or
(b) varying its molecular weight; and/or
(c) adding suitable plasticizers; and/or
(d) choosing the copolymers.

In the above discussion modulus of elasticity is defined as the ratio of the tensile stress (forced per unit area), over strain (proportional elongation), and it is expressed in units of pressure (psi, pounds per square inch).

The self-healing" effect is further enhanced provided:

(a) the modulus of elasticity of the overlayer elastomer ($ME_o$) matches, or is lower than, the modulus of elasticity of the base layer ($ME_B$), The lowest value that $MB_o$ can take is that corresponding to an elastomeric gel, as long as the gel bonds adhesively to the base layer. In that case the thickness of the overlayer is determined by the elastomer gel used; and (b) the viscosity of the overlay elastomer (in its liquid state, on coating), is as low as required to form a cured overlayer of minimum thickness of 0.01 mm by dip-coating the base layer.

For example, Dow Corning RTV #734 has a viscosity of 450 poise at 25 degrees C. Diluted to 50% by volume with Cyclomethicone, its viscosity becomes comparable (as measured by a simple viscosity comparison arrangement), to that of 10% wt. solution of Glycerol at the same temperature, which corresponds to a viscosity of approximately 2 poise. When a microscope glass slide is dip-coated in the 50% elastomer dispersion and permitted to vulcanize in its vertical position, it forms a silicone rubber coating of 0.01 mm at its thinnest section.

The liquid coating material of the overlayer must "wet" the cured base layer (i.e., angle of contact 90 degrees), and to bond adhesively to it upon curing, otherwise the dual-layer elastomeric article becomes delaminated in the first stretch-relax cycle. Thus, in general, a silicone rubber dispersion bonds adhesively to a natural latex rubber surface after vulcanization, whereas natural latex rubber does not bond to a silicone rubber surface. In addition, the dispersant should be chemically compatible with the natural rubber, so that it does not chemically attack the natural rubber.

While preferred embodiments of this invention have been illustrated and described, variations and modifications may be apparent to those skilled in the art. Therefore, I do not wish to be limited thereto and ask that the scope and breadth of this invention be determined from the claims which follow rather than the above description.

What I claim is:

1. A mold for fabricating an article, comprising:
    a continuous surface for receiving material which at least partially solidifies thereon to form a first layer of said article;
    said continuous surface defining a three-dimensional pattern for said article;
    means for controlling the area of said surface to change the size of said three-dimensional pattern without distorting the relative dimensional relationship of the component segments forming said pattern whereby material may be deposited on and bonded to said first layer to form a second layer which at least partially solidifies so that when said article is removed from said mold a state of relative expansive/compressive tension is created at the bond interface between said first and second layers; and said means for controlling the area of said surface comprises a hollow expandable elastic core including a pressurizable envelope fabricated from an inelastic flexible material positioned within said core for creating a differential pressure between the interior of said hollow expandable elastic core and the exterior thereof and for limiting the expansion of said core and said three-dimensional pattern.

2. A mold as defined in claim 1 wherein said continuous surface defining a three-dimensional pattern is the outer surface of said core.

3. A mold as defined in claim 1, comprising:
    a rigid inner core including fluid passages therein.

4. A mold as defined in claim 1, comprising:
    an open-cell foam elastomeric inner core.

5. A mold as defined in claim 1, comprising a second pressurizable envelope fabricated from an inelastic flexible material positioned within said core and containing said pressurizable envelope for limiting the expansion of said core and said three-dimensional pattern to a size greater than allowed by said pressurizable envelope.

6. A mold as defined in claim 1 wherein said means for creating a differential pressure between the interior of said hollow expandable elastic core and the exterior thereof comprises a means for hydraulically pressurizing the interior of said core.

7. A mold as defined in claim 1 wherein said means for creating a differential pressure between the interior of said hollow expandable elastic core and the exterior thereof comprises a means for pneumatically pressurizing the interior of said core.

8. A mold as defined in claim 1 wherein said means for creating a differential pressure between the interior of said hollow expandable elastic core and the exterior thereof comprises:
    a pressurizable container encompassing said core; and means for evacuating said container.

9. A mold as defined in claim 1 wherein said means for creating a differential pressure between the interior of said hollow expandable elastic core and the exterior thereof comprises:
    a pressurizable container encompassing said core; and means for pressurizing said container.

10. A mold as defined in claim 1 wherein said continuous surface defining a three-dimensional pattern for said article is electrically conductive.

11. A mold as defined in claim 1, comprising:
    an expansible electrically conductive coating on said continuous surface defining a three-dimensional pattern for said article.

12. A method for fabricating an article, including the steps of:
    applying a curable liquid elastomeric material to a mold core;
    uniformly expanding said mold core and said elastomeric material after said elastomeric material is at least partially cured;
    coating said elastomeric material on said mold core with a second material;

returning said mold core and said elastomeric material to their original relaxed state.

13. A method for fabricating an article as defined in claim 12, wherein said second material is an elastomeric material having properties different than said elastomeric material, including the further step of:
allowing said mold core and said elastomeric material to return to their original relaxed state after said second elastomeric material applied to said elastomeric material is at least partially cured 14. A method for fabricating an article as defined in claim 12, wherein the step of uniformly expanding a mold core includes the step of pressurizing the interior of said mold core to a pressure greater than the ambient pressure of the mold core exterior.

15. A method for fabricating an article as defined in claim 12, wherein the step of uniformly expanding a mold core includes the step or evacuating the interior of said mold core to a pressure less than the ambient pressure of the mold core exterior.

16. A method for fabricating an article, including the steps of:
applying a curable liquid elastomeric material to a mold core;
after said elastomeric material is at least partially cured, inflating an inelastic envelope within said mold core to uniformly expand said mold core and said elastomeric material coating said expanded elastomeric material on said mold core with a curable liquid elastomeric material;
returning said expanded mold core and said expanded elastomeric material to their original relaxed state after said elastomeric material applied to said expanded elastomeric material is at least partially cured.

17. A method for fabricating an article as defined in claim 16, including the further step of:
inflating a first inelastic envelope positioned within said inelastic envelope to uniformly expand said mold core to a first state of expansion before said step of applying a curable liquid elastomeric material to said mold core.

* * * * *